(12) United States Patent
Kerr et al.

(10) Patent No.: US 12,201,524 B2
(45) Date of Patent: Jan. 21, 2025

(54) METHODS AND SYSTEMS FOR RAPID RETRACTION OF A TRANSCATHETER HEART VALVE DELIVERY SYSTEM

(71) Applicant: Neovasc Tiara Inc., Richmond (CA)

(72) Inventors: Ian Fraser Kerr, Vancouver (CA); Karen Tsoek-Ji Wong, Richmond (CA); Colin Alexander Nyuli, Vancouver (CA); Randy Matthew Lane, Langley (CA)

(73) Assignee: Neovasc Tiara Inc., Richmond (CA)

( * ) Notice: Subject to any disclaimer, the term of this patent is extended or adjusted under 35 U.S.C. 154(b) by 78 days.

(21) Appl. No.: 17/902,433

(22) Filed: Sep. 2, 2022

(65) Prior Publication Data

US 2023/0074473 A1    Mar. 9, 2023

Related U.S. Application Data

(63) Continuation of application No. 16/796,157, filed on Feb. 20, 2020, now Pat. No. 11,464,631, which is a
(Continued)

(51) Int. Cl.
| | | |
|---|---|---|
| *A61F 2/24* | (2006.01) | |
| *A61M 29/02* | (2006.01) | |
| *A61F 2/95* | (2013.01) | |

(52) U.S. Cl.
CPC .......... *A61F 2/2433* (2013.01); *A61F 2/2427* (2013.01); *A61F 2/2436* (2013.01);
(Continued)

(58) Field of Classification Search
CPC .... A61F 2/2433; A61F 2/2427; A61F 2/2436; A61M 29/02
See application file for complete search history.

(56) References Cited

U.S. PATENT DOCUMENTS

| | | | |
|---|---|---|---|
| 2,967,856 A | 1/1961 | Coover, Jr. et al. | |
| 6,911,039 B2 * | 6/2005 | Shiu | A61F 2/966 623/1.23 |

(Continued)

FOREIGN PATENT DOCUMENTS

| | | |
|---|---|---|
| AU | 2017361296 B2 | 9/2022 |
| CA | 2874219 C | 7/2020 |

(Continued)

OTHER PUBLICATIONS

"U.S. Appl. No. 15/819,512, Non Final Office Action mailed Nov. 22, 2019", 15 pgs.
(Continued)

*Primary Examiner* — Tuan V Nguyen
(74) *Attorney, Agent, or Firm* — Schwegman Lundberg & Woessner, P.A.

(57) ABSTRACT

Methods for the rapid retraction of trans-catheter heart valve delivery systems are provided. A rapid retraction trans-catheter heart valve delivery system comprises a catheter based delivery system. The delivery system has internal mechanisms that allow for the controlled deployment of a heart valve prosthesis, as well as mechanisms that allow for quickly closing the catheter once the heart valve prosthesis has been implanted. This rapid retraction ability allows for reduced procedural durations and thus reduced risk to the patient.

23 Claims, 15 Drawing Sheets

Related U.S. Application Data continuation of application No. 15/819,512, filed on Nov. 21, 2017, now abandoned.

(60) Provisional application No. 62/424,910, filed on Nov. 21, 2016.

(52) U.S. Cl.
CPC ........... *A61M 29/02* (2013.01); *A61F 2/9517* (2020.05); *A61F 2250/0064* (2013.01)

(56) References Cited

U.S. PATENT DOCUMENTS

| | | | |
|---|---|---|---|
| 8,579,964 B2 | 11/2013 | Lane et al. | |
| 11,464,631 B2 | 10/2022 | Kerr et al. | |
| 2007/0168014 A1 | 7/2007 | Jimenez et al. | |
| 2009/0254165 A1 | 10/2009 | Tabor et al. | |
| 2011/0015616 A1 | 1/2011 | Straubinger et al. | |
| 2011/0264191 A1 | 10/2011 | Rothstein | |
| 2011/0319989 A1 | 12/2011 | Lane et al. | |
| 2012/0179243 A1 | 7/2012 | Yang et al. | |
| 2012/0310332 A1 | 12/2012 | Murray et al. | |
| 2013/0231735 A1 | 9/2013 | Deem et al. | |
| 2013/0297011 A1 | 11/2013 | Morris et al. | |
| 2014/0067050 A1 | 3/2014 | Costello et al. | |
| 2015/0134054 A1 | 5/2015 | Morrissey | |
| 2015/0297378 A1 | 10/2015 | Senness et al. | |
| 2015/0306358 A1 | 10/2015 | Duffy et al. | |
| 2018/0140419 A1 | 5/2018 | Kerr et al. | |
| 2020/0188105 A1 | 6/2020 | Kerr et al. | |

FOREIGN PATENT DOCUMENTS

| | | |
|---|---|---|
| CN | 103501730 A | 1/2014 |
| CN | 109996581 A | 7/2019 |
| CN | 109996581 B | 10/2021 |
| CN | 113893064 A | 1/2022 |
| DE | 10103955 B4 | 11/2001 |
| DE | 10033858 B4 | 1/2002 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 202013011734 U1 | 4/2014 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |

(56) References Cited

FOREIGN PATENT DOCUMENTS

| | | | |
|---|---|---|---|
| EP | 1173117 | B1 | 7/2007 |
| EP | 1434615 | B1 | 7/2007 |
| EP | 1465546 | B1 | 7/2007 |
| EP | 1499366 | B1 | 7/2007 |
| EP | 1225948 | B1 | 8/2007 |
| EP | 1819304 | A2 | 8/2007 |
| EP | 1519962 | B1 | 9/2007 |
| EP | 1337285 | B1 | 10/2007 |
| EP | 1112042 | B1 | 11/2007 |
| EP | 1148821 | B1 | 11/2007 |
| EP | 1143882 | B1 | 12/2007 |
| EP | 1330189 | B1 | 12/2007 |
| EP | 1489996 | B1 | 12/2007 |
| EP | 1296618 | B1 | 1/2008 |
| EP | 1401356 | B1 | 1/2008 |
| EP | 1629795 | B1 | 1/2008 |
| EP | 1128786 | B1 | 2/2008 |
| EP | 1616532 | B1 | 2/2008 |
| EP | 1289447 | B1 | 3/2008 |
| EP | 1895942 | A2 | 3/2008 |
| EP | 1115353 | B1 | 5/2008 |
| EP | 1330190 | B1 | 5/2008 |
| EP | 1383448 | B1 | 6/2008 |
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1625548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511455 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |

(56) References Cited

FOREIGN PATENT DOCUMENTS

| | | | |
|---|---|---|---|
| EP | 1768610 B1 | 12/2010 |
| EP | 1827314 B1 | 12/2010 |
| EP | 1940321 B1 | 12/2010 |
| EP | 1964532 B1 | 12/2010 |
| EP | 2078498 B1 | 12/2010 |
| EP | 1600182 B1 | 1/2011 |
| EP | 1617789 B1 | 1/2011 |
| EP | 1663332 B1 | 1/2011 |
| EP | 2147659 B1 | 1/2011 |
| EP | 2268231 A2 | 1/2011 |
| EP | 2273951 A1 | 1/2011 |
| EP | 1187582 B1 | 2/2011 |
| EP | 1450733 B1 | 2/2011 |
| EP | 1803421 B1 | 2/2011 |
| EP | 1833425 B1 | 2/2011 |
| EP | 2029053 B1 | 2/2011 |
| EP | 2068770 B1 | 2/2011 |
| EP | 1441784 B1 | 3/2011 |
| EP | 1534177 B1 | 3/2011 |
| EP | 1893132 B1 | 3/2011 |
| EP | 1951153 B1 | 3/2011 |
| EP | 2289467 A1 | 3/2011 |
| EP | 2299938 A2 | 3/2011 |
| EP | 1359978 B1 | 4/2011 |
| EP | 1667750 B1 | 4/2011 |
| EP | 1718249 B1 | 4/2011 |
| EP | 1903989 B1 | 4/2011 |
| EP | 2018122 B1 | 4/2011 |
| EP | 1610728 B1 | 5/2011 |
| EP | 2105110 B1 | 5/2011 |
| EP | 1347717 B1 | 6/2011 |
| EP | 2331018 A1 | 6/2011 |
| EP | 1347791 B1 | 7/2011 |
| EP | 1862128 B1 | 7/2011 |
| EP | 2120795 B1 | 7/2011 |
| EP | 2229920 B1 | 7/2011 |
| EP | 1637087 B1 | 8/2011 |
| EP | 2153799 B1 | 8/2011 |
| EP | 2247263 B1 | 8/2011 |
| EP | 2349095 A1 | 8/2011 |
| EP | 2349097 A1 | 8/2011 |
| EP | 2358307 A1 | 8/2011 |
| EP | 1441672 B1 | 9/2011 |
| EP | 1625832 B1 | 9/2011 |
| EP | 2173279 B1 | 9/2011 |
| EP | 2367505 A1 | 9/2011 |
| EP | 2160150 B1 | 10/2011 |
| EP | 2370138 A2 | 10/2011 |
| EP | 1626679 B1 | 11/2011 |
| EP | 1719476 B1 | 11/2011 |
| EP | 1928355 B1 | 11/2011 |
| EP | 2237747 B1 | 11/2011 |
| EP | 2381895 A2 | 11/2011 |
| EP | 2389121 A1 | 11/2011 |
| EP | 1572031 B1 | 12/2011 |
| EP | 1603493 B1 | 12/2011 |
| EP | 1945109 B1 | 12/2011 |
| EP | 1998688 B1 | 12/2011 |
| EP | 2393442 A2 | 12/2011 |
| EP | 2395944 A1 | 12/2011 |
| EP | 1443877 B1 | 1/2012 |
| EP | 2400922 A1 | 1/2012 |
| EP | 1281375 B1 | 2/2012 |
| EP | 1699501 B1 | 2/2012 |
| EP | 1788984 B1 | 2/2012 |
| EP | 1833415 B1 | 2/2012 |
| EP | 1952785 B1 | 2/2012 |
| EP | 2055266 B1 | 2/2012 |
| EP | 2205184 B1 | 2/2012 |
| EP | 2416736 A1 | 2/2012 |
| EP | 1337188 B1 | 3/2012 |
| EP | 1443974 B1 | 3/2012 |
| EP | 1542623 B1 | 3/2012 |
| EP | 1942835 B1 | 3/2012 |
| EP | 2074964 B1 | 3/2012 |
| EP | 2244661 B1 | 3/2012 |
| EP | 2273928 B1 | 3/2012 |
| EP | 2427144 A1 | 3/2012 |
| EP | 2429455 A1 | 3/2012 |
| EP | 1410336 B1 | 4/2012 |
| EP | 1749544 B1 | 4/2012 |
| EP | 2119417 B1 | 4/2012 |
| EP | 2152330 B1 | 4/2012 |
| EP | 2231069 B1 | 4/2012 |
| EP | 2437688 A1 | 4/2012 |
| EP | 2020958 B1 | 5/2012 |
| EP | 2218425 B1 | 5/2012 |
| EP | 2445450 A2 | 5/2012 |
| EP | 2453970 A2 | 5/2012 |
| EP | 1411847 B1 | 6/2012 |
| EP | 1727499 B1 | 6/2012 |
| EP | 2082690 B1 | 6/2012 |
| EP | 1740747 B1 | 7/2012 |
| EP | 1861044 B1 | 7/2012 |
| EP | 2052699 B1 | 7/2012 |
| EP | 2470121 A2 | 7/2012 |
| EP | 2471492 A1 | 7/2012 |
| EP | 1887975 B1 | 8/2012 |
| EP | 2000116 B1 | 8/2012 |
| EP | 2222247 B1 | 8/2012 |
| EP | 2486894 A1 | 8/2012 |
| EP | 1605870 B1 | 9/2012 |
| EP | 1887980 B1 | 9/2012 |
| EP | 2497445 A1 | 9/2012 |
| EP | 1740126 B1 | 10/2012 |
| EP | 1865889 B1 | 10/2012 |
| EP | 2033593 B1 | 10/2012 |
| EP | 2124824 B1 | 10/2012 |
| EP | 2139431 B1 | 10/2012 |
| EP | 2506777 A1 | 10/2012 |
| EP | 2512952 A2 | 10/2012 |
| EP | 1430853 B1 | 11/2012 |
| EP | 1928512 B1 | 11/2012 |
| EP | 2008615 B1 | 11/2012 |
| EP | 2088965 B1 | 11/2012 |
| EP | 2520249 A1 | 11/2012 |
| EP | 2522307 A1 | 11/2012 |
| EP | 1557138 B1 | 12/2012 |
| EP | 1924221 B1 | 12/2012 |
| EP | 2023859 B1 | 12/2012 |
| EP | 2250970 B1 | 12/2012 |
| EP | 2285317 B1 | 12/2012 |
| EP | 2537486 A1 | 12/2012 |
| EP | 1494731 B1 | 1/2013 |
| EP | 1610752 B1 | 1/2013 |
| EP | 1796597 B1 | 1/2013 |
| EP | 1919397 B1 | 1/2013 |
| EP | 1942834 B1 | 1/2013 |
| EP | 2015709 B1 | 1/2013 |
| EP | 2079400 B1 | 1/2013 |
| EP | 2238947 B1 | 1/2013 |
| EP | 2241287 B1 | 1/2013 |
| EP | 2359774 B1 | 1/2013 |
| EP | 2538878 A1 | 1/2013 |
| EP | 2538883 A1 | 1/2013 |
| EP | 1512383 B1 | 2/2013 |
| EP | 1578474 B1 | 2/2013 |
| EP | 1648339 B1 | 2/2013 |
| EP | 1750622 B1 | 2/2013 |
| EP | 1994482 B1 | 2/2013 |
| EP | 2250975 B1 | 2/2013 |
| EP | 2257242 B1 | 2/2013 |
| EP | 2265225 B1 | 2/2013 |
| EP | 2558032 A1 | 2/2013 |
| EP | 1659992 B1 | 3/2013 |
| EP | 1701668 B1 | 3/2013 |
| EP | 2151216 B1 | 3/2013 |
| EP | 2340075 B1 | 3/2013 |
| EP | 2568924 A2 | 3/2013 |
| EP | 1781183 B1 | 4/2013 |
| EP | 1786367 B1 | 4/2013 |
| EP | 1850795 B1 | 4/2013 |
| EP | 1861041 B1 | 4/2013 |
| EP | 2319458 B1 | 4/2013 |

(56) References Cited

FOREIGN PATENT DOCUMENTS

| | | | |
|---|---|---|---|
| EP | 2526898 | B1 | 4/2013 |
| EP | 2537487 | B1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611388 | A2 | 7/2013 |
| EP | 2611389 | A2 | 7/2013 |
| EP | 2618781 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2698129 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2285316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |
| EP | 2785281 | A1 | 10/2014 |
| EP | 2793743 | A1 | 10/2014 |
| EP | 2793749 | A1 | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |
| EP | 2303185 | B1 | 12/2014 |
| EP | 2334857 | B1 | 12/2014 |
| EP | 2365840 | B1 | 12/2014 |
| EP | 2420207 | B1 | 12/2014 |
| EP | 2422750 | B1 | 12/2014 |
| EP | 2707073 | B1 | 12/2014 |
| EP | 1768630 | B1 | 1/2015 |
| EP | 2254515 | B1 | 1/2015 |
| EP | 2641569 | B1 | 1/2015 |
| EP | 2709559 | B1 | 1/2015 |
| EP | 2825203 | A1 | 1/2015 |
| EP | 1903990 | B1 | 2/2015 |
| EP | 2255753 | B1 | 2/2015 |
| EP | 2335649 | B1 | 2/2015 |
| EP | 2522308 | B1 | 2/2015 |
| EP | 2591754 | B1 | 2/2015 |

(56) References Cited

FOREIGN PATENT DOCUMENTS

| | | | |
|---|---|---|---|
| EP | 2835112 | A1 | 2/2015 |
| EP | 1861045 | B1 | 3/2015 |
| EP | 2029057 | B1 | 3/2015 |
| EP | 2193761 | B1 | 3/2015 |
| EP | 2379010 | B1 | 3/2015 |
| EP | 2416737 | B1 | 3/2015 |
| EP | 1791495 | B1 | 4/2015 |
| EP | 2298252 | B1 | 4/2015 |
| EP | 2536359 | B1 | 4/2015 |
| EP | 2538879 | B1 | 4/2015 |
| EP | 2609894 | B1 | 4/2015 |
| EP | 2693984 | B1 | 4/2015 |
| EP | 2712633 | B1 | 4/2015 |
| EP | 2747707 | B1 | 4/2015 |
| EP | 2862546 | A1 | 4/2015 |
| EP | 2863842 | A1 | 4/2015 |
| EP | 1465555 | B1 | 5/2015 |
| EP | 1924224 | B1 | 5/2015 |
| EP | 1992369 | B1 | 5/2015 |
| EP | 2192875 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2023079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2916781 | A2 | 9/2015 |
| EP | 2919712 | A1 | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 2948103 | A2 | 12/2015 |
| EP | 2959866 | A1 | 12/2015 |
| EP | 1991168 | B1 | 1/2016 |
| EP | 2254512 | B1 | 1/2016 |
| EP | 2422748 | B1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967858 | A2 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |

(56) References Cited

FOREIGN PATENT DOCUMENTS

| | | | |
|---|---|---|---|
| EP | 2572676 | B1 | 4/2016 |
| EP | 2606852 | B1 | 4/2016 |
| EP | 2621408 | B1 | 4/2016 |
| EP | 2626040 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3052611 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1292478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068346 | A1 | 9/2016 |
| EP | 3068645 | A1 | 9/2016 |
| EP | 3071148 | A1 | 9/2016 |
| EP | 3071149 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2934387 | B1 | 10/2016 |
| EP | 3076901 | A1 | 10/2016 |
| EP | 3079633 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3102150 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |

(56) References Cited

FOREIGN PATENT DOCUMENTS

| | | | |
|---|---|---|---|
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 3158975 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3160396 | A1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3175823 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |

(56) References Cited

FOREIGN PATENT DOCUMENTS

| | | | |
|---|---|---|---|
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 3220857 | A1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3245980 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2670351 | A4 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277221 | A1 | 2/2018 |
| EP | 3277222 | A1 | 2/2018 |
| EP | 3280358 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3298970 | A1 | 3/2018 |
| EP | 3298987 | A1 | 3/2018 |
| EP | 3298988 | A1 | 3/2018 |
| EP | 2209440 | B1 | 4/2018 |

(56) References Cited

FOREIGN PATENT DOCUMENTS

| | | | |
|---|---|---|---|
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | B1 | 4/2018 |
| EP | 3095394 | B1 | 4/2018 |
| EP | 3128927 | A4 | 4/2018 |
| EP | 3134033 | B1 | 4/2018 |
| EP | 3137146 | A4 | 4/2018 |
| EP | 3280482 | A4 | 4/2018 |
| EP | 3302297 | A2 | 4/2018 |
| EP | 3302362 | A1 | 4/2018 |
| EP | 3307208 | A1 | 4/2018 |
| EP | 3308745 | A1 | 4/2018 |
| EP | 3310301 | A1 | 4/2018 |
| EP | 3311774 | A1 | 4/2018 |
| EP | 3311775 | A1 | 4/2018 |
| EP | 3311783 | A1 | 4/2018 |
| EP | 272277 | B1 | 5/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3322383 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334378 | A1 | 6/2018 |
| EP | 3334380 | A1 | 6/2018 |
| EP | 3334381 | A1 | 6/2018 |
| EP | 3335670 | A1 | 6/2018 |
| EP | 3337412 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |
| EP | 3340923 | A1 | 7/2018 |
| EP | 3340932 | A1 | 7/2018 |
| EP | 3340934 | A1 | 7/2018 |
| EP | 3340936 | A1 | 7/2018 |
| EP | 3340945 | A1 | 7/2018 |
| EP | 3342355 | A1 | 7/2018 |
| EP | 3342377 | A1 | 7/2018 |
| EP | 3344158 | A1 | 7/2018 |
| EP | 3346952 | A1 | 7/2018 |
| EP | 3347182 | A1 | 7/2018 |
| EP | 3348235 | A1 | 7/2018 |
| EP | 3349693 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 3361991 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 3370650 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |

(56) References Cited

FOREIGN PATENT DOCUMENTS

| | | | |
|---|---|---|---|
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 3388027 | A1 | 10/2018 |
| EP | 3389557 | A1 | 10/2018 |
| EP | 3390706 | A1 | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3397206 | A1 | 11/2018 |
| EP | 3398562 | A1 | 11/2018 |
| EP | 3400908 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3107495 | A1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3410984 | A1 | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3427695 | A1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3409454 | A4 | 2/2019 |
| EP | 3435919 | A1 | 2/2019 |
| EP | 3441045 | A1 | 2/2019 |
| EP | 3442469 | A1 | 2/2019 |
| EP | 3443937 | A1 | 2/2019 |
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3449969 | A1 | 3/2019 |
| EP | 3454785 | A1 | 3/2019 |
| EP | 3454786 | A1 | 3/2019 |
| EP | 3454789 | A1 | 3/2019 |
| EP | 3454794 | A1 | 3/2019 |
| EP | 3454795 | A1 | 3/2019 |
| EP | 3457987 | A1 | 3/2019 |
| EP | 3457988 | A1 | 3/2019 |
| EP | 3457990 | A1 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 1703870 | B1 | 5/2019 |
| EP | 1708642 | B1 | 5/2019 |

(56) References Cited

FOREIGN PATENT DOCUMENTS

| | | | |
|---|---|---|---|
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316819 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487451 | A1 | 5/2019 |
| EP | 3487452 | A1 | 5/2019 |
| EP | 3488822 | A1 | 5/2019 |
| EP | 1624792 | B1 | 6/2019 |
| EP | 1737694 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490657 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 3515365 | A1 | 7/2019 |
| EP | 3517075 | A1 | 7/2019 |
| EP | 1861043 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534845 | A2 | 9/2019 |
| EP | 3535010 | A1 | 9/2019 |
| EP | 3538026 | A1 | 9/2019 |
| EP | 3538027 | A1 | 9/2019 |
| EP | 3539508 | A1 | 9/2019 |
| EP | 3539509 | A1 | 9/2019 |
| EP | 3541325 | A1 | 9/2019 |
| EP | 3542758 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |

(56) References Cited

FOREIGN PATENT DOCUMENTS

| | | | |
|---|---|---|---|
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3545905 A1 | 10/2019 |
| EP | 3547936 A1 | 10/2019 |
| EP | 3547966 A1 | 10/2019 |
| EP | 3549555 A1 | 10/2019 |
| EP | 3549556 A1 | 10/2019 |
| EP | 3552585 A1 | 10/2019 |
| EP | 3554424 A1 | 10/2019 |
| EP | 3556323 A1 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |
| EP | 3142607 B1 | 11/2019 |
| EP | 3167850 B1 | 11/2019 |
| EP | 3397205 B1 | 11/2019 |
| EP | 3563799 A1 | 11/2019 |
| EP | 3563806 A1 | 11/2019 |
| EP | 3570779 A1 | 11/2019 |
| EP | 3572045 A1 | 11/2019 |
| EP | 3572117 A1 | 11/2019 |
| EP | 3479800 A4 | 12/2019 |
| EP | 3576677 A1 | 12/2019 |
| EP | 3579761 A2 | 12/2019 |
| EP | 3579788 A1 | 12/2019 |
| EP | 3582697 A1 | 12/2019 |
| EP | 3583922 A1 | 12/2019 |
| EP | 3445443 A4 | 1/2020 |
| EP | 3590471 A1 | 1/2020 |
| EP | 3590472 A1 | 1/2020 |
| EP | 3592284 A1 | 1/2020 |
| EP | 3592288 A1 | 1/2020 |
| EP | 3592289 A1 | 1/2020 |
| EP | 3593763 A1 | 1/2020 |
| EP | 3600156 A1 | 2/2020 |
| EP | 3600159 A1 | 2/2020 |
| EP | 3606443 A1 | 2/2020 |
| EP | 3606472 A1 | 2/2020 |
| EP | 2241287 B2 | 3/2020 |
| EP | 2376013 B1 | 3/2020 |
| EP | 2911593 B1 | 3/2020 |
| EP | 2995279 B1 | 3/2020 |
| EP | 3009103 B1 | 3/2020 |
| EP | 3038664 B1 | 3/2020 |
| EP | 3167848 B1 | 3/2020 |
| EP | 3175822 B1 | 3/2020 |
| EP | 3179660 B1 | 3/2020 |
| EP | 3280479 B1 | 3/2020 |
| EP | 3616651 A1 | 3/2020 |
| EP | 3619136 A1 | 3/2020 |
| EP | 3626208 A1 | 3/2020 |
| EP | 1667614 B2 | 4/2020 |
| EP | 2119417 B2 | 4/2020 |
| EP | 2155114 B1 | 4/2020 |
| EP | 2299937 B1 | 4/2020 |
| EP | 2331016 B1 | 4/2020 |
| EP | 2376013 B8 | 4/2020 |
| EP | 2413843 B1 | 4/2020 |
| EP | 2854705 B1 | 4/2020 |
| EP | 2918249 B1 | 4/2020 |
| EP | 2922593 B1 | 4/2020 |
| EP | 2950753 B1 | 4/2020 |
| EP | 2967810 B1 | 4/2020 |
| EP | 3110367 B1 | 4/2020 |
| EP | 3111888 B1 | 4/2020 |
| EP | 3128927 B1 | 4/2020 |
| EP | 3134032 B1 | 4/2020 |
| EP | 3142606 B1 | 4/2020 |
| EP | 3278025 B1 | 4/2020 |
| EP | 3300696 B1 | 4/2020 |
| EP | 3316823 B1 | 4/2020 |
| EP | 3334487 B1 | 4/2020 |
| EP | 3342355 B1 | 4/2020 |
| EP | 3373863 B1 | 4/2020 |
| EP | 3459498 B1 | 4/2020 |
| EP | 3470105 B1 | 4/2020 |
| EP | 3628239 A1 | 4/2020 |
| EP | 3628274 A1 | 4/2020 |
| EP | 3632338 A1 | 4/2020 |
| EP | 3636312 A1 | 4/2020 |
| EP | 3639792 A1 | 4/2020 |
| EP | 3639888 A1 | 4/2020 |
| EP | 3643273 A1 | 4/2020 |
| EP | 1895942 B1 | 5/2020 |
| EP | 2120821 B1 | 5/2020 |
| EP | 2437688 B1 | 5/2020 |
| EP | 2785281 B1 | 5/2020 |
| EP | 2852354 B1 | 5/2020 |
| EP | 2884906 B1 | 5/2020 |
| EP | 2999412 B1 | 5/2020 |
| EP | 3060174 B1 | 5/2020 |
| EP | 3071147 B1 | 5/2020 |
| EP | 3104812 B1 | 5/2020 |
| EP | 3139861 B1 | 5/2020 |
| EP | 3232989 B1 | 5/2020 |
| EP | 3294219 B1 | 5/2020 |
| EP | 3298970 B1 | 5/2020 |
| EP | 3302366 B1 | 5/2020 |
| EP | 3323389 B1 | 5/2020 |
| EP | 3332744 B1 | 5/2020 |
| EP | 3402440 B1 | 5/2020 |
| EP | 3417813 B1 | 5/2020 |
| EP | 3417831 B1 | 5/2020 |
| EP | 3457987 B1 | 5/2020 |
| EP | 3484413 B1 | 5/2020 |
| EP | 3531975 B1 | 5/2020 |
| EP | 3644866 A1 | 5/2020 |
| EP | 3646822 A1 | 5/2020 |
| EP | 3646824 A1 | 5/2020 |
| EP | 3646825 A1 | 5/2020 |
| EP | 3648706 A1 | 5/2020 |
| EP | 3656354 A1 | 5/2020 |
| EP | 1648339 B2 | 6/2020 |
| EP | 2072027 B1 | 6/2020 |
| EP | 2331016 B8 | 6/2020 |
| EP | 2616007 B1 | 6/2020 |
| EP | 2967856 B1 | 6/2020 |
| EP | 3042635 B1 | 6/2020 |
| EP | 3060165 B1 | 6/2020 |
| EP | 3280338 B1 | 6/2020 |
| EP | 3283010 B1 | 6/2020 |
| EP | 3400908 B1 | 6/2020 |
| EP | 3494928 B1 | 6/2020 |
| EP | 3498225 B1 | 6/2020 |
| EP | 3583920 B1 | 6/2020 |
| EP | 3659553 A1 | 6/2020 |
| EP | 3661429 A1 | 6/2020 |
| EP | 3668450 A1 | 6/2020 |
| EP | 3668452 A1 | 6/2020 |
| EP | 3669828 A1 | 6/2020 |
| EP | 3669829 A1 | 6/2020 |
| EP | 2271284 B1 | 7/2020 |
| EP | 2291145 B1 | 7/2020 |
| EP | 2512952 B1 | 7/2020 |
| EP | 2558029 B1 | 7/2020 |
| EP | 2693985 B1 | 7/2020 |
| EP | 2858708 B1 | 7/2020 |

(56) References Cited

FOREIGN PATENT DOCUMENTS

| | | | |
|---|---|---|---|
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3672532 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 3685802 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |
| EP | 3634255 | B1 | 8/2020 |
| EP | 3689299 | A1 | 8/2020 |
| EP | 3691567 | A1 | 8/2020 |
| EP | 3697342 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3720363 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3272117 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3530828 | B1 | 12/2020 |
| EP | 3539510 | B1 | 12/2020 |
| EP | 3544548 | B1 | 12/2020 |
| EP | 3545906 | B1 | 12/2020 |
| EP | 3593763 | B1 | 12/2020 |
| EP | 3744291 | A1 | 12/2020 |
| EP | 3749254 | A1 | 12/2020 |
| EP | 3753535 | A1 | 12/2020 |
| EP | 3756623 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3758651 | A1 | 1/2021 |
| EP | 3760164 | A1 | 1/2021 |
| EP | 3763331 | A1 | 1/2021 |
| EP | 2273951 | B1 | 2/2021 |
| EP | 2379008 | B1 | 2/2021 |
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |

(56) References Cited

FOREIGN PATENT DOCUMENTS

| | | | |
|---|---|---|---|
| EP | 3506855 B1 | 3/2021 |
| EP | 3531979 B1 | 3/2021 |
| EP | 3535010 B1 | 3/2021 |
| EP | 3581151 B1 | 3/2021 |
| EP | 3590472 B1 | 3/2021 |
| EP | 3593760 B1 | 3/2021 |
| EP | 3646825 B1 | 3/2021 |
| EP | 3649985 B1 | 3/2021 |
| EP | 3787561 A1 | 3/2021 |
| EP | 3790501 A1 | 3/2021 |
| EP | 3791795 A1 | 3/2021 |
| EP | 3791828 A1 | 3/2021 |
| EP | 3796873 A1 | 3/2021 |
| EP | 3796875 A1 | 3/2021 |
| EP | 1734872 B1 | 4/2021 |
| EP | 2594230 B1 | 4/2021 |
| EP | 2624785 B1 | 4/2021 |
| EP | 2670349 B1 | 4/2021 |
| EP | 2793752 B1 | 4/2021 |
| EP | 2823769 B1 | 4/2021 |
| EP | 2964152 B1 | 4/2021 |
| EP | 3253331 B1 | 4/2021 |
| EP | 3290004 B1 | 4/2021 |
| EP | 3311778 B1 | 4/2021 |
| EP | 3367979 B1 | 4/2021 |
| EP | 3454794 B1 | 4/2021 |
| EP | 3487420 B1 | 4/2021 |
| EP | 3558165 B1 | 4/2021 |
| EP | 3616651 B1 | 4/2021 |
| EP | 3619136 B1 | 4/2021 |
| EP | 3626208 B1 | 4/2021 |
| EP | 3632379 B1 | 4/2021 |
| EP | 3646823 B1 | 4/2021 |
| EP | 3646824 B1 | 4/2021 |
| EP | 3653173 B1 | 4/2021 |
| EP | 1951155 B1 | 5/2021 |
| EP | 2073755 B1 | 5/2021 |
| EP | 2948100 B1 | 5/2021 |
| EP | 3099270 B1 | 5/2021 |
| EP | 3150172 B1 | 5/2021 |
| EP | 3178445 B1 | 5/2021 |
| EP | 3310301 B1 | 5/2021 |
| EP | 3582697 B1 | 5/2021 |
| EP | 3592295 B1 | 5/2021 |
| EP | 3639888 B1 | 5/2021 |
| EP | 3669828 B1 | 5/2021 |
| EP | 2471492 B1 | 6/2021 |
| EP | 2486894 B1 | 6/2021 |
| EP | 2750630 B1 | 6/2021 |
| EP | 3247312 B1 | 6/2021 |
| EP | 3294215 B1 | 6/2021 |
| EP | 3323353 B1 | 6/2021 |
| EP | 3360513 B1 | 6/2021 |
| EP | 3488821 B1 | 6/2021 |
| EP | 3549555 B1 | 6/2021 |
| EP | 3576677 B1 | 6/2021 |
| EP | 3632338 B1 | 6/2021 |
| EP | 2381895 B1 | 7/2021 |
| EP | 2611389 B1 | 7/2021 |
| EP | 2779945 B1 | 7/2021 |
| EP | 3193740 B1 | 7/2021 |
| EP | 3206629 B1 | 7/2021 |
| EP | 3277222 B1 | 7/2021 |
| EP | 3400907 B1 | 7/2021 |
| EP | 3435919 B1 | 7/2021 |
| EP | 3522800 B1 | 7/2021 |
| EP | 3539508 B1 | 7/2021 |
| EP | 3539509 B1 | 7/2021 |
| EP | 3572044 B1 | 7/2021 |
| EP | 3592289 B1 | 7/2021 |
| EP | 3668450 B1 | 7/2021 |
| EP | 3681439 B1 | 7/2021 |
| EP | 3691567 B1 | 7/2021 |
| EP | 3849472 A1 | 7/2021 |
| EP | 2558032 B1 | 8/2021 |
| EP | 2992857 B1 | 8/2021 |
| EP | 2994075 B1 | 8/2021 |
| EP | 3038539 B1 | 8/2021 |
| EP | 3287099 B1 | 8/2021 |
| EP | 3348235 B1 | 8/2021 |
| EP | 3643273 B1 | 8/2021 |
| EP | 3646822 B1 | 8/2021 |
| EP | 3658215 B1 | 8/2021 |
| EP | 3659553 B1 | 8/2021 |
| EP | 3723665 B1 | 8/2021 |
| EP | 3744290 B1 | 8/2021 |
| EP | 3860530 A1 | 8/2021 |
| EP | 2040645 B1 | 9/2021 |
| EP | 2329796 B1 | 9/2021 |
| EP | 3125827 B1 | 9/2021 |
| EP | 3137146 B1 | 9/2021 |
| EP | 3288494 B1 | 9/2021 |
| EP | 3288497 B1 | 9/2021 |
| EP | 3446660 B1 | 9/2021 |
| EP | 3454784 B1 | 9/2021 |
| EP | 3456293 B1 | 9/2021 |
| EP | 3457989 B1 | 9/2021 |
| EP | 3496664 B1 | 9/2021 |
| EP | 3503848 B1 | 9/2021 |
| EP | 3512465 B1 | 9/2021 |
| EP | 3544664 B1 | 9/2021 |
| EP | 3568089 B1 | 9/2021 |
| EP | 3592288 B1 | 9/2021 |
| EP | 3606472 B1 | 9/2021 |
| EP | 3669829 B1 | 9/2021 |
| EP | 3672528 B1 | 9/2021 |
| EP | 3833302 A4 | 9/2021 |
| EP | 3870110 A1 | 9/2021 |
| EP | 2249711 B1 | 10/2021 |
| EP | 2538883 B1 | 10/2021 |
| EP | 2723273 B1 | 10/2021 |
| EP | 3119351 B1 | 10/2021 |
| EP | 3267946 B1 | 10/2021 |
| EP | 3275404 B1 | 10/2021 |
| EP | 3280482 B1 | 10/2021 |
| EP | 3334381 B1 | 10/2021 |
| EP | 3639792 B1 | 10/2021 |
| EP | 3886763 A1 | 10/2021 |
| EP | 3892240 A1 | 10/2021 |
| EP | 3900679 A1 | 10/2021 |
| EP | 2331018 B1 | 11/2021 |
| EP | 2429455 B1 | 11/2021 |
| EP | 2538878 B1 | 11/2021 |
| EP | 2699302 B1 | 11/2021 |
| EP | 2706958 B1 | 11/2021 |
| EP | 2892467 B1 | 11/2021 |
| EP | 2999434 B1 | 11/2021 |
| EP | 3024527 B1 | 11/2021 |
| EP | 3061422 B1 | 11/2021 |
| EP | 3107500 B1 | 11/2021 |
| EP | 3110468 B1 | 11/2021 |
| EP | 3154474 B1 | 11/2021 |
| EP | 3213715 B1 | 11/2021 |
| EP | 3256076 B1 | 11/2021 |
| EP | 3288499 B1 | 11/2021 |
| EP | 3360514 B1 | 11/2021 |
| EP | 3429507 B1 | 11/2021 |
| EP | 3445443 B1 | 11/2021 |
| EP | 3454785 B1 | 11/2021 |
| EP | 3505077 B1 | 11/2021 |
| EP | 3672529 B1 | 11/2021 |
| EP | 3760164 B1 | 11/2021 |
| EP | 3912595 A1 | 11/2021 |
| EP | 3912596 A1 | 11/2021 |
| EP | 2358307 B1 | 12/2021 |
| EP | 2765954 B1 | 12/2021 |
| EP | 2777608 B1 | 12/2021 |
| EP | 2991584 B1 | 12/2021 |
| EP | 3283011 B1 | 12/2021 |
| EP | 3288479 B1 | 12/2021 |
| EP | 3344167 B1 | 12/2021 |
| EP | 3410987 B1 | 12/2021 |
| EP | 3481339 B1 | 12/2021 |
| EP | 3482718 B1 | 12/2021 |

(56) References Cited

FOREIGN PATENT DOCUMENTS

| | | |
|---|---|---|
| EP | 3490465 B1 | 12/2021 |
| EP | 3498224 B1 | 12/2021 |
| EP | 3503846 B1 | 12/2021 |
| EP | 3592284 B1 | 12/2021 |
| EP | 3624705 B1 | 12/2021 |
| EP | 3749254 B1 | 12/2021 |
| EP | 3914191 A1 | 12/2021 |
| EP | 2400922 B1 | 1/2022 |
| EP | 2545885 B1 | 1/2022 |
| EP | 2747708 B1 | 1/2022 |
| EP | 2763708 B1 | 1/2022 |
| EP | 2994072 B1 | 1/2022 |
| EP | 3220856 B1 | 1/2022 |
| EP | 3288498 B1 | 1/2022 |
| EP | 3534840 B1 | 1/2022 |
| EP | 3558169 B1 | 1/2022 |
| EP | 3668452 B1 | 1/2022 |
| EP | 3682854 B1 | 1/2022 |
| EP | 3697346 B1 | 1/2022 |
| EP | 3700467 B1 | 1/2022 |
| EP | 3740162 B1 | 1/2022 |
| EP | 3294218 B1 | 2/2022 |
| EP | 3457988 B1 | 2/2022 |
| EP | 3481336 B1 | 2/2022 |
| EP | 3673925 B1 | 2/2022 |
| EP | 3689299 B1 | 2/2022 |
| EP | 3753535 B1 | 2/2022 |
| EP | 3860530 B1 | 2/2022 |
| EP | 2623068 B1 | 3/2022 |
| EP | 2866737 B1 | 3/2022 |
| EP | 3160396 B1 | 3/2022 |
| EP | 3193782 B1 | 3/2022 |
| EP | 3334380 B1 | 3/2022 |
| EP | 3355800 B1 | 3/2022 |
| EP | 3479797 B1 | 3/2022 |
| EP | 3479800 B1 | 3/2022 |
| EP | 3628274 B1 | 3/2022 |
| EP | 3679894 B1 | 3/2022 |
| EP | 3787561 B1 | 3/2022 |
| EP | 3791795 B1 | 3/2022 |
| EP | 3962415 A1 | 3/2022 |
| EP | 3253332 B1 | 6/2022 |
| EP | 3298988 B1 | 6/2022 |
| EP | 3661436 B1 | 6/2022 |
| EP | 3790501 B1 | 6/2022 |
| EP | 3849472 B1 | 6/2022 |
| EP | 4014928 A1 | 6/2022 |
| EP | 2621409 B1 | 7/2022 |
| EP | 2787926 B1 | 7/2022 |
| EP | 2838473 B1 | 7/2022 |
| EP | 2950752 B1 | 7/2022 |
| EP | 3060171 B1 | 7/2022 |
| EP | 3206631 B1 | 7/2022 |
| EP | 3245980 B1 | 7/2022 |
| EP | 3256073 B1 | 7/2022 |
| EP | 3311783 B1 | 7/2022 |
| EP | 3347182 B1 | 7/2022 |
| EP | 3389557 B1 | 7/2022 |
| EP | 3463120 B1 | 7/2022 |
| EP | 3579788 B1 | 7/2022 |
| EP | 3756623 B1 | 7/2022 |
| EP | 3796872 B1 | 7/2022 |
| EP | 3796876 B1 | 7/2022 |
| EP | 2313152 B1 | 8/2022 |
| EP | 2688516 B1 | 8/2022 |
| EP | 2849678 B1 | 8/2022 |
| EP | 2950751 B1 | 8/2022 |
| EP | 2964153 B1 | 8/2022 |
| EP | 3019092 B1 | 8/2022 |
| EP | 3184082 B1 | 8/2022 |
| EP | 3231395 B1 | 8/2022 |
| EP | 3266417 B1 | 8/2022 |
| EP | 3407834 B1 | 8/2022 |
| EP | 3458136 B1 | 8/2022 |
| EP | 3459499 B1 | 8/2022 |
| EP | 3471662 B1 | 8/2022 |
| EP | 3484412 B1 | 8/2022 |
| EP | 3534841 B1 | 8/2022 |
| EP | 3541328 B1 | 8/2022 |
| EP | 3672532 B1 | 8/2022 |
| EP | 3718509 B1 | 8/2022 |
| EP | 3769721 B1 | 8/2022 |
| EP | 3789077 B1 | 8/2022 |
| EP | 3908228 B1 | 8/2022 |
| EP | 3915493 B1 | 8/2022 |
| EP | 3967274 B1 | 8/2022 |
| EP | 2670351 B1 | 9/2022 |
| EP | 2777617 B1 | 9/2022 |
| EP | 2810620 B1 | 9/2022 |
| EP | 2922592 B1 | 9/2022 |
| EP | 3038567 B1 | 9/2022 |
| EP | 3096713 B1 | 9/2022 |
| EP | 3220857 B1 | 9/2022 |
| EP | 3448315 B1 | 9/2022 |
| EP | 3481335 B1 | 9/2022 |
| EP | 3520715 B1 | 9/2022 |
| EP | 3645065 B1 | 9/2022 |
| EP | 3737336 B1 | 9/2022 |
| EP | 2104470 B1 | 10/2022 |
| EP | 2536353 B1 | 10/2022 |
| EP | 2991588 B1 | 10/2022 |
| EP | 3043755 B1 | 10/2022 |
| EP | 3288491 B1 | 10/2022 |
| EP | 3466373 B1 | 10/2022 |
| EP | 3552585 B1 | 10/2022 |
| EP | 3791828 B1 | 10/2022 |
| EP | 3914191 B1 | 10/2022 |
| EP | 2538882 B1 | 11/2022 |
| EP | 2698129 B1 | 11/2022 |
| EP | 2959866 B1 | 11/2022 |
| EP | 3175823 B1 | 11/2022 |
| EP | 3280358 B1 | 11/2022 |
| EP | 3340923 B1 | 11/2022 |
| EP | 3478224 B1 | 11/2022 |
| EP | 3490659 B1 | 11/2022 |
| EP | 3744291 B1 | 11/2022 |
| FR | 2815844 B1 | 1/2003 |
| FR | 2826863 B1 | 9/2003 |
| FR | 2828091 B1 | 11/2003 |
| FR | 2847800 B1 | 10/2005 |
| FR | 2858543 B1 | 2/2006 |
| FR | 2828263 B1 | 5/2007 |
| FR | 2874812 B1 | 6/2007 |
| FR | 2874813 B1 | 6/2007 |
| FR | 2883721 B1 | 6/2007 |
| FR | 2894131 B1 | 12/2008 |
| FR | 2899096 B1 | 12/2008 |
| FR | 2910269 B1 | 2/2009 |
| FR | 2909857 B1 | 3/2009 |
| FR | 2906454 B1 | 4/2009 |
| FR | 2906998 B1 | 4/2009 |
| FR | 2913879 B1 | 6/2009 |
| FR | 2916959 B1 | 9/2009 |
| FR | 2892939 B1 | 1/2010 |
| FR | 2915678 B1 | 4/2010 |
| FR | 2930137 B1 | 4/2010 |
| FR | 2915903 B1 | 6/2010 |
| FR | 2916627 B1 | 9/2010 |
| FR | 2920664 B1 | 9/2010 |
| FR | 2932376 B1 | 4/2011 |
| FR | 2947716 B1 | 9/2011 |
| FR | 2945440 B1 | 12/2012 |
| FR | 2951549 B1 | 8/2013 |
| FR | 2964855 B1 | 10/2013 |
| FR | 2977792 B1 | 10/2013 |
| FR | 2980968 B1 | 12/2013 |
| FR | 2986149 B1 | 12/2014 |
| FR | 2997288 B1 | 1/2015 |
| FR | 2998167 B1 | 1/2015 |
| FR | 2996747 B1 | 2/2015 |
| FR | 2996748 B1 | 2/2015 |
| FR | 3004638 B1 | 5/2015 |
| FR | 2982763 B1 | 7/2015 |
| FR | 2991162 B1 | 7/2015 |

(56) References Cited

FOREIGN PATENT DOCUMENTS

| | | |
|---|---|---|
| FR | 3006582 B1 | 7/2015 |
| FR | 3001121 B1 | 1/2016 |
| FR | 2998166 B1 | 2/2016 |
| FR | 3021862 B1 | 5/2016 |
| FR | 3004917 B1 | 6/2016 |
| FR | 3006884 B1 | 6/2016 |
| FR | 3023704 B1 | 8/2016 |
| FR | 3008885 B1 | 12/2016 |
| FR | 3033494 B1 | 3/2017 |
| FR | 3057154 B1 | 10/2018 |
| FR | 3058631 B1 | 1/2019 |
| FR | 3058632 B1 | 1/2019 |
| FR | 3060292 B1 | 1/2019 |
| FR | 3063631 B1 | 3/2019 |
| FR | 3020265 B1 | 9/2019 |
| FR | 3072013 B1 | 9/2019 |
| GB | 243370 A | 8/1926 |
| GB | 2407146 B | 4/2006 |
| GB | 2398245 B | 3/2007 |
| GB | 2433700 B | 12/2007 |
| GB | 2478498 B | 7/2012 |
| GB | 2530487 B | 12/2016 |
| GB | 2517609 B | 5/2017 |
| GB | 2538749 B | 8/2017 |
| GB | 2538072 B | 11/2017 |
| GB | 2536538 B | 7/2018 |
| GB | 2548891 B | 7/2018 |
| WO | WO-2018090148 A1 | 5/2018 |

OTHER PUBLICATIONS

"U.S. Appl. No. 15/819,512, Preliminary Amendment filed Nov. 28, 2017", 3 pgs.

"U.S. Appl. No. 15/819,512, Response filed Oct. 28, 2019 to Restriction Requirement mailed Aug. 28, 2019", 8 pgs.

"U.S. Appl. No. 15/819,512, Restriction Requirement mailed Aug. 28, 2019", 8 pgs.

"U.S. Appl. No. 16/796,157, Notice of Allowance mailed Jun. 2, 2022", 14 pgs.

"U.S. Appl. No. 16/796,157, Response filed May 9, 2022 to Restriction Requirement mailed Mar. 7, 2022", 9 pgs.

"U.S. Appl. No. 16/796,157, Restriction Requirement mailed Mar. 7, 2022", 8 pgs.

"U.S. Appl. No. 16/796,157, Supplemental Notice of Allowability mailed Jun. 10, 2022", 2 pgs.

"Australian Application Serial No. 2017361296, First Examination Report mailed Apr. 27, 2022", 3 pgs.

"Australian Application Serial No. 2017361296, Response filed Sep. 8, 2022 to First Examination Report mailed Apr. 27, 2022", 16 pgs.

"Canadian Application Serial No. 3,042,588, Voluntary Amendment Filed Nov. 9, 2022", 14 pgs.

"Chinese Application Serial No. 2017800720409, Office Action mailed Mar. 1, 2021", with machine translation, 14 pgs.

"Chinese Application Serial No. 2017800720409, Response filed Jun. 1, 2021 to Office Action mailed Mar. 1, 2021", w/English claims, 13 pgs.

"Chinese Application Serial No. 2017800720409, Response filed Jul. 13, 2021 to Telephone Consultation on Jul. 6, 2021", with machine translation and English translation of claims, 56 pgs.

"Chinese Application Serial No. 202111153690.0, Voluntary Amendment filed Apr. 13, 2022", w/ English Claims, 12 pgs.

"European Application Serial No. 17870820.2, Extended European Search Report mailed May 19, 2020", 7 pgs.

"European Application Serial No. 17870820.2, Response filed Dec. 18, 2020 to Extended European Search Report mailed May 19, 2020", 15 pgs.

"International Application Serial No. PCT/CA2017/051387, International Preliminary Report on Patentability mailed May 31, 2019", 7 pgs.

"International Application Serial No. PCT/CA2017/051387, International Search Report mailed Feb. 2, 2018", 7 pgs.

"International Application Serial No. PCT/CA2017/051387, Written Opinion mailed Feb. 2, 2018", 5 pgs.

U.S. Appl. No. 15/819,512, filed Nov. 21, 2017, Methods and Systems for Rapid Retraction of a Transcatheter Heart Valve Delivery System.

U.S. Appl. No. 16/796,157 U.S. Pat. No. 11,464,631, filed Feb. 20, 2020, Methods and Systems for Rapid Retraction of a Transcatheter Heart Valve Delivery System.

"Australian Application Serial No. 2022291583, First Examination Report mailed Apr. 19, 2024", 3 pgs.

"Australian Application Serial No. 2022291583, Response filed Jun. 20, 2024 to First Examination Report mailed Apr. 19, 2024", 10 pgs.

"Canadian Application Serial No. 3,042,588, Examiners Rule 86(2) Report mailed Apr. 19, 2024", 4 pgs.

"Chinese Application Serial No. 202111153690.0, Office Action mailed Jan. 4, 2024", W/English Translation, 15 pgs.

"European Application Serial No. 17870820.2, Communication Pursuant to Article 94(3) EPC mailed Apr. 26, 2024", 5 pgs.

"Canadian Application Serial No. 3,042,588, Response filed Jul. 11, 2024 to Examiners Rule 86(2) Report mailed Apr. 19, 2024", 12 pgs.

"Chinese Application Serial No. 202111153690.0, Office Action mailed Jul. 8, 2024", w English Translation, 17 pgs.

"Chinese Application Serial No. 202111153690.0, Response filed May 6, 2024 to Office Action mailed Jan. 4, 2024", W English claims, 17 pgs.

\* cited by examiner

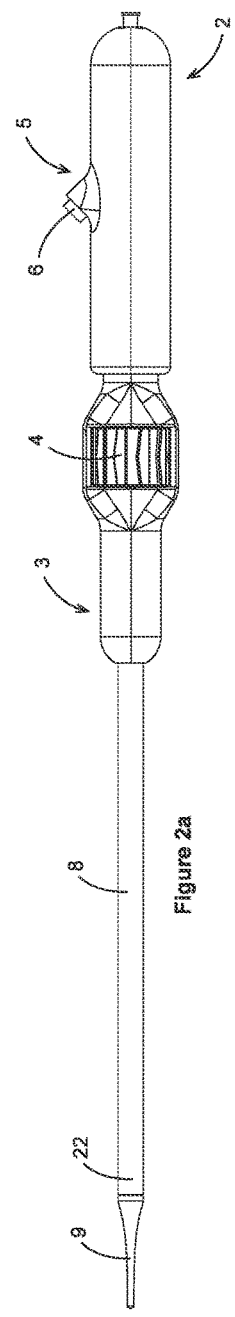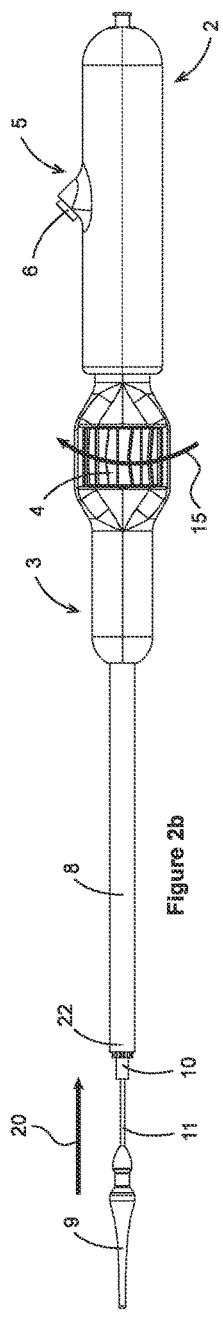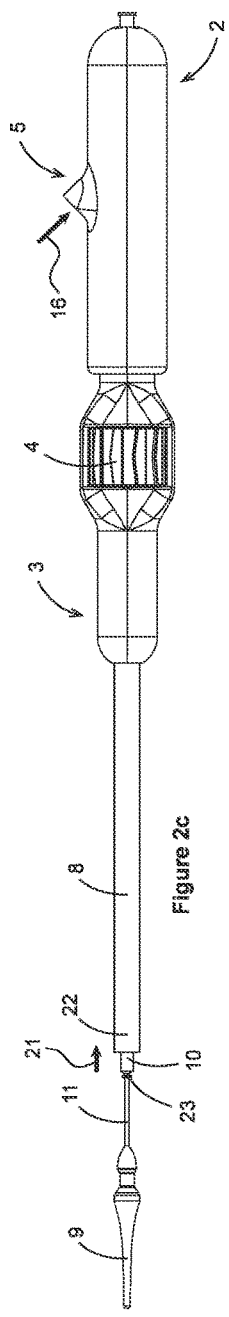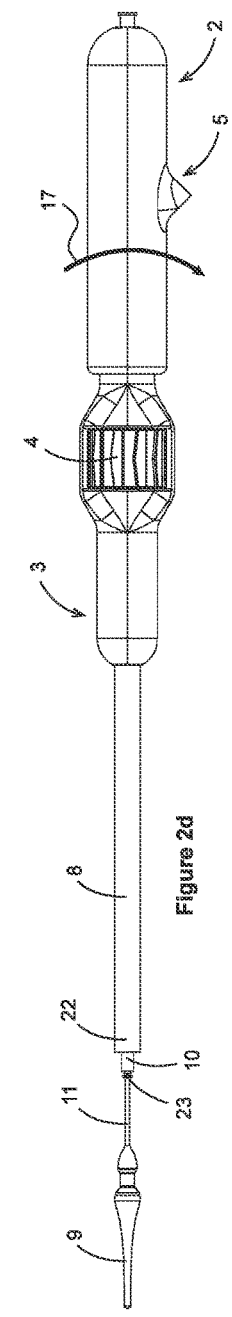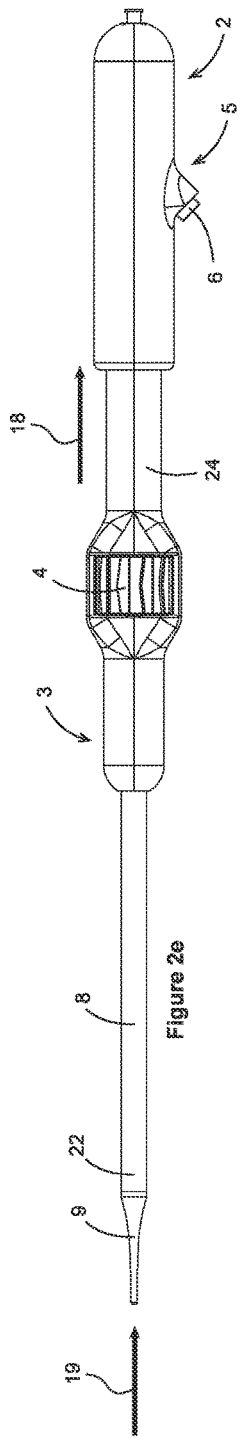

METHODS AND SYSTEMS FOR RAPID RETRACTION OF A TRANSCATHETER HEART VALVE DELIVERY SYSTEM

CROSS-REFERENCE

The present application is a continuation of U.S. patent application Ser. No. 16/796,157, filed Feb. 20, 2020, which application is a continuation of U.S. patent application Ser. No. 15/819,512, filed Nov. 21, 2017, which application claims priority to U.S. Provisional Patent Application No. 62/424,910, filed on Nov. 21, 2016, which is herein incorporated by reference in its entirety.

The present application is related to: U.S. Pat. No. 8,579,964 filed Apr. 28, 2011; and also related to U.S. Publication Nos. 2013/0211508 filed Nov. 16, 2012; 2014/0052237 filed Feb. 8, 2013; 2014/0155990 filed May 29, 2013; 2014/0257467 filed Mar. 3, 2014; and 2014/0343669 filed Apr. 1, 2014; the entire contents of each of which is incorporated herein by reference.

BACKGROUND OF THE INVENTION

1. Field of the Invention

Mitral regurgitation, also known as mitral insufficiency or mitral incompetence is a heart condition in which the mitral valve does not close properly thereby resulting in abnormal leakage of blood retrograde from the left ventricle through the mitral valve back upstream into the left atrium. Persistent mitral regurgitation can result in congestive heart failure, a costly and often fatal condition. Traditional surgical repair of the valve generally results in a good clinical outcome but requires open heart surgery and a lengthy and costly hospital stay along with an extended recovery period. More recently, minimally invasive procedures have been developed to deliver a prosthetic heart valve percutaneously over a catheter through the patient's vasculature to the heart, or by using a transapical procedure to introduce the prosthesis through the chest wall and through the apex of the heart to the treatment site. An exemplary prosthesis includes any of the embodiments described in U.S. Pat. No. 8,579,964, the entire contents of which are incorporated herein by reference. These prostheses and delivery procedures appear to be promising, but there is yet opportunity to improve procedural outcomes by minimizing the duration of the procedure, from first contact with the delivery system by an operator to final withdrawal of the delivery system and wound closure in the patient. Therefore, it would be desirable to provide improved devices, systems, and methods that reduce the amount of time needed to remove the delivery system from the patient, improve ease of use, speed up the procedure, and reduce risk. At least some of these objectives will be met by the exemplary embodiments described herein.

2. Description of the Background Art

U.S. Pat. No. 8,579,964 discloses an exemplary prosthetic heart valve and trans-catheter delivery system, the entire contents previously incorporated herein by reference.

BRIEF SUMMARY

The present disclosure generally relates to medical systems, devices and methods, and more particularly relates to prostheses and delivery systems such as heart valve delivery systems that may be used to implant a prosthesis such as a valve, including a prosthetic mitral valve, a heart valve, or any other valve. The present disclosure emphasizes exemplary embodiments of a prosthetic mitral valve and delivery system, but one of skill in the art will appreciate that this is not intended to be limiting.

In many embodiments, trans-catheter methods and systems of deploying prosthetic heart valves and rapid retraction of the delivery system are provided. In certain embodiments, the delivery system comprises a trans-apical delivery system that may be used to implant a prosthetic heart valve into anatomical position by way of an incision in the apex of the heart. The trans-apical delivery system may comprise a system of catheters that may be concentrically nested upon one another and that, when combined, may retain a compressed heart valve prosthesis. Removal of the constraint provided by certain catheters may then facilitate deployment of the heart valve prosthesis into the heart. Further embodiments of the trans-apical delivery system that may be used in any of the delivery systems disclose herein may allow for the closure of the delivery catheters at an enhanced speed, such as by way of translation of catheter components within each other in the opposite direction to that required for deployment operation. The operation of such delivery systems may be facilitated through the use of actuator mechanisms such as button mechanisms that may be in communication with linkage systems, or actuator mechanisms such as button mechanisms that may be in communication with flexible members, or even pin coupled components that simplify use.

Further embodiments herein may include delivery systems that allow for alternative implantation pathways such as through the inferior or superior vena cava, the aorta, or the atria.

In an aspect of the present disclosure, a method of rapidly retracting a delivery system comprises providing a delivery system, the delivery system having a plurality of catheters used to deliver a heart valve prosthesis, providing a controllable deployment mechanism, the controllable deployment mechanism having the ability to preferentially release a prosthesis from the catheter, and actuating the controllable deployment mechanism thereby releasing the prosthesis from the catheter. The method may also comprise providing a rapid retraction mechanism, the rapid retraction mechanism having the ability to rapidly close the catheter, actuating the rapid retracting mechanism thereby rapidly closing the catheter.

The method may comprise trans-apically introducing the delivery system into an apex of a heart, or transseptally delivering the delivery system to a heart, delivering the delivery system to the heart via a subclavian vein, delivering the delivery system to the heart via an aorta, or delivering the delivery system to the heart via a left atrium or a right atrium.

Actuating the rapid retraction mechanism may comprise actuating a button and linkage. The rapid retraction mechanism may comprise a threaded region and interference member, and the method may further comprise constraining movement of the rapid retraction mechanism with the threaded region and interference member. The rapid retraction mechanism may comprise a flexible interference member, and the method may further comprise deflecting the flexible interference member. The rapid retraction mechanism may comprise a pin and pin-hole link assembly, and the method may comprise removing the pin from the pin-hole link assembly.

In another aspect of the present disclosure, a delivery device for delivering a prosthesis comprises a first actuation mechanism for controlling movement of a delivery catheter, wherein the delivery catheter may be configured to carry a prosthesis therein, and wherein actuation of the first actuation mechanism may move the delivery catheter away from the prosthesis thereby at least partially removing a constraint therefrom, and a deployment mechanism for controlling release of the prosthesis from an anchoring catheter, the anchoring catheter disposed at least partially in the delivery catheter, and wherein actuation of the deployment mechanism may move the anchoring catheter away from the prosthesis thereby releasing a constraint therefrom. The delivery system may also comprise an inner guidewire catheter having a tapered distal tip, the inner guidewire catheter disposed in the anchoring catheter, and a rapid retraction mechanism for controlling movement of the delivery catheter relative to the tapered distal tip, wherein actuation of the rapid retraction mechanism closes the delivery device such that a proximal end of the distal tip abuts against a distal end of the delivery catheter thereby forming a smooth continuous outer surface of the delivery device.

The actuation mechanism may comprise a thumbwheel. The deployment mechanism may comprise an actuatable button with a linkage coupled thereto. The rapid retraction mechanism may comprise a threaded region and interference member, a flexible interference member, or a pin and pinhole linkage assembly.

In another aspect of the present disclosure, a system for delivering a prosthesis comprise the delivery device described above and a prosthesis such as a prosthetic mitral valve.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 2A-2E illustrate schematic side views of an operational sequence of a trans-apical delivery system configured to allow for rapid retraction.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
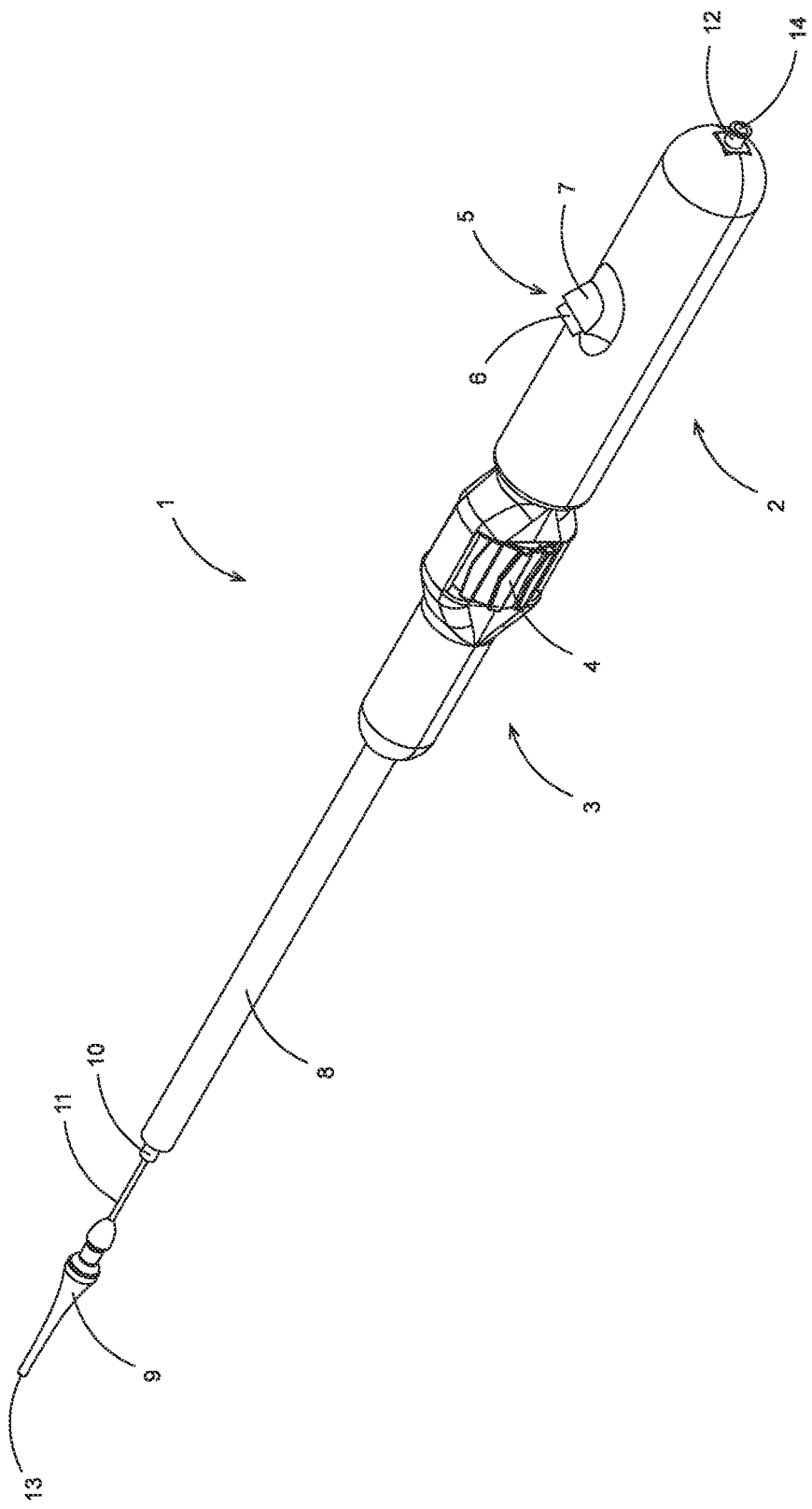
FIG. 1 shows a perspective view of a trans-apical delivery system configured to allow for rapid retraction.

FIG. 1 shows a perspective view of a trans-apical delivery system 1 which may be configured to allow for delivery of a prosthesis such as a prosthetic heart valve with rapid retraction of the delivery system after the prosthesis has been delivered, whereby rapid retraction herein may comprise the expedient removal of the delivery catheter 8 and dilating tip 9 from the apex of a patient's heart (not shown) or other treatment region of the patient. The trans-apical delivery system 1 may be comprised of a dilating tapered tip 9 which is delivered directly into the apex of a patient's heart (not shown), a delivery catheter 8 (sometimes referred to as a sheath catheter), a handle assembly including a distal handle 3, a proximal external handle 2, and an actuator mechanism such as a thumbwheel 4 therebetween which may be configured to actuate said delivery catheter 8 in order to cause it to slidably translate away from the dilating tip 9 into an open configuration or open position. When the trans-apical delivery system is in the open position, a space for a prosthetic heart valve 11 or any other prosthesis may be defined between the dilating tip 9 and the distal edge of the delivery catheter 8 (best seen in FIG. 2A). An innermost lumen can be defined between the guidewire lumen inlet 13, located at the distal most end of the dilating tip 9, and the guidewire lumen outlet 14 which may be located within a connector such as a needle hub 12 having a Luer connector at its proximal end, at the proximal most portion of the proximal external handle 2. The guidewire lumen may extend through the guidewire catheter (sometimes also referred to as the dilator catheter) which may be axially and concentrically disposed under the other catheters including bell catheter 10. The guidewire catheter may be referred to as a guidewire catheter. Any of the features describing the delivery catheter 8 may be applied to any of the delivery catheter embodiments disclosed herein. Similarly, any of the prosthetic heart valve features described for prosthetic heart valve may apply to the prostheses disclosed herein.

Also shown in FIG. 1 is an embodiment of an actuation mechanism 5, which can allow a user to control the final release of a prosthesis such as a prosthetic heart valve from the delivery system, and can enable further mechanical actions that will be described below. The actuation mechanism 5 may be comprised of any actuator such as a button 6, and a disposed in a housing 7 which describes a space wherein the button 6 may translate. The mechanical details behind the translation will be further described below.

Turning now to FIG. 2A-2E, an operational sequence of a trans-apical delivery system 1 configured to allow for rapid retraction is presented. FIG. 2A shows the delivery system 1 in the closed configuration where all catheters may be concentrically disposed over one another, and the distal leading edge 22 of delivery catheter 8 may be disposed against the proximal end of dilating tip 9 to form a smooth continuous outer surface. A prosthesis such as a prosthetic heart valve may be loaded and disposed in the space 11 and constrained by the catheters. The closed configuration may be configured for trans-apical delivery of the prosthesis to the treatment region in the heart. FIG. 2B shows an arrow indicating translation 20 of the distal leading edge of the delivery catheter 22 in the proximal direction. An arrow indicating rotation 15 of the thumbwheel 4 is also shown, and when the thumbwheel 4 is rotated, proximal translation of the distal leading edge of the delivery catheter 8 may occur by way of internal component mechanical relationships, such as those described within U.S. Pat. No. 8,579, 964 (also referred to herein as the '964 patent), which is incorporated herein by reference. For example, FIGS. 11-15C of the '964 patent describe one exemplary embodiment of a delivery system having features which may apply to the present exemplary embodiment, and FIGS. 16-20 of the '964 patent describe another exemplary embodiment having features which may apply to the present exemplary embodiment. Rotation of the thumbwheel in the opposite direction may move the delivery catheter 8 in the opposite direction, distally.

FIG. 2C shows an arrow indicating radially inward translation 16 of an actuator, here a button 6. An arrow indicating proximal translation 21 of the distal leading edge 22 of the delivery catheter 8 is also shown, and also when the button 6 is depressed radially inwardly, the leading edge of the bell catheter 10 may translate proximally away from and off of an anchoring catheter (sometimes referred as a hub catheter), anchoring tip 23, as further described in the '964 patent, for example, in FIGS. 16-20. By releasing the leading edge of the bell catheter 10 (similarly referred to as a bell catheter) from the anchoring catheter anchoring tip 23, a prosthesis such as a prosthetic heart valve (not shown) may be preferentially released. The internal mechanics of this component relationship will be further described in detail below.

FIG. 2D depicts the operation of the rapid retraction functionality of the herein disclosed trans-apical delivery system 1. By maintaining pressure on the button 6, the proximal external handle 2 may be rotated as depicted by the arrow indicating rotation 17. By rotating the proximal external handle 2 for one 360° rotation in a first direction (clockwise with respect to the operator), the handle can become disengaged from the middle section of the internal handle 24 and thus may be free to translate proximally over internal handle 24, as depicted by the arrow indicating translation 18 (FIG. 2E). The dilator tip 9 by way of the connector such as needle hub 12 (FIG. 5), and anchoring catheter 50 (FIG. 5) by way of the externally threaded portion of anchoring catheter 51 (FIG. 5) may be mated to the proximal external handle 2. The bell catheter proximal end 68 (FIG. 5) may be fastened to the catheter carriage 30 (FIG. 5), which may be translated along with the proximal external handle 2, and depicted by an arrow indicating translation 19 (FIG. 2E). This movement may allow the proximal end of the dilator tip to butt up against the distal end of the delivery catheter 8 to form a smooth continuous surface when the delivery system is in a closed configuration.

Figure 3A:
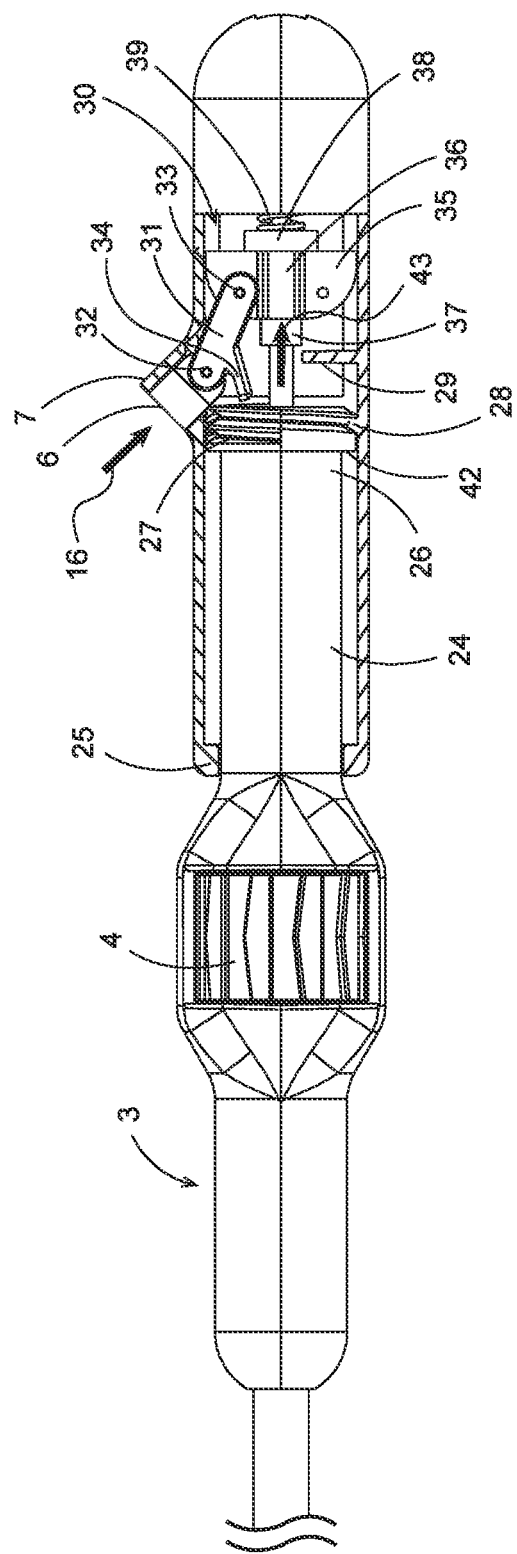
FIGS. 3A-3D illustrate partial cross-sectional breakout views of an operational sequence of a trans-apical delivery system configured to allow for rapid retraction.

FIGS. 3A-3D more clearly illustrate some of the actuation mechanism. Turning now to FIG. 3A, there is illustrated the first view of a sequence of views of an operational sequence of a trans-apical delivery system that is configured to allow for rapid retraction of the delivery system 1, depicted by way of cross-sectional breakout. The middle section of the internal handle 24 is shown, which acts as a support structure for the proximal external handle 2 to slide thereover. Specifically, an internal circular rib 25 may traverse the distal-most portion of the inner diameter of the proximal external handle 2, and in conjunction with the external threads 27 of the middle section of the internal handle 24 as well as an external circular flange 42, may provide support and location for the middle section of the internal handle 24 to translate within the proximal external handle 2 (shown in FIG. 5). In operable communication with the external threads 27 of the middle section of the internal handle 24 may be internal threads 28 of the proximal external handle 2, which can allow for relative rotation and controlled translation between the two handles without binding or cocking, prior to disengagement. An additional feature of embodiments of this device which may be used in any embodiment of a delivery system disclosed herein, with specific regards to the external threads 27 of the middle section of the internal handle 24 is an internal slot 40 (FIG. 4A), the details of which will be described further below.

Figure 4A:
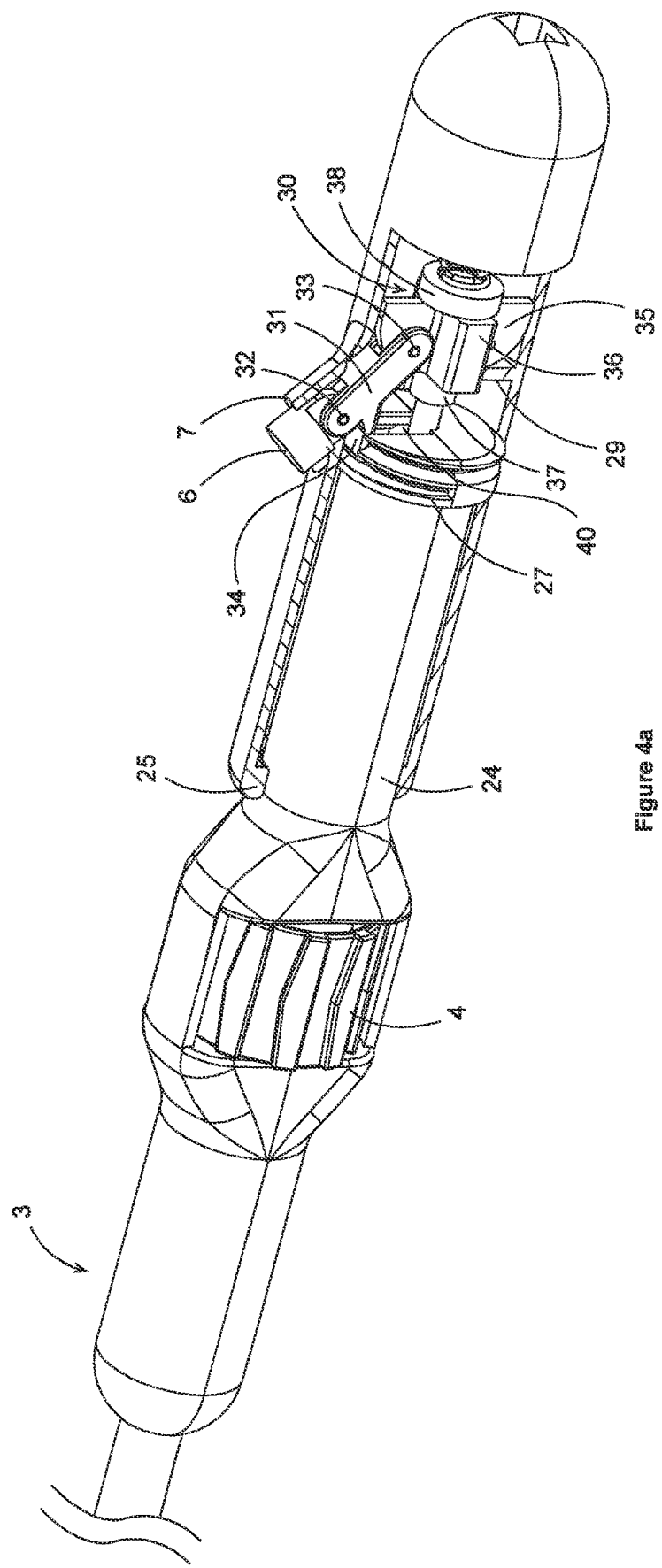
FIGS. 4A-4B illustrate isometric partial cross-sectional breakout views of a sequence of action of an internal mechanism within a trans-apical delivery system configured to allow for rapid retraction.
Figure 4B:
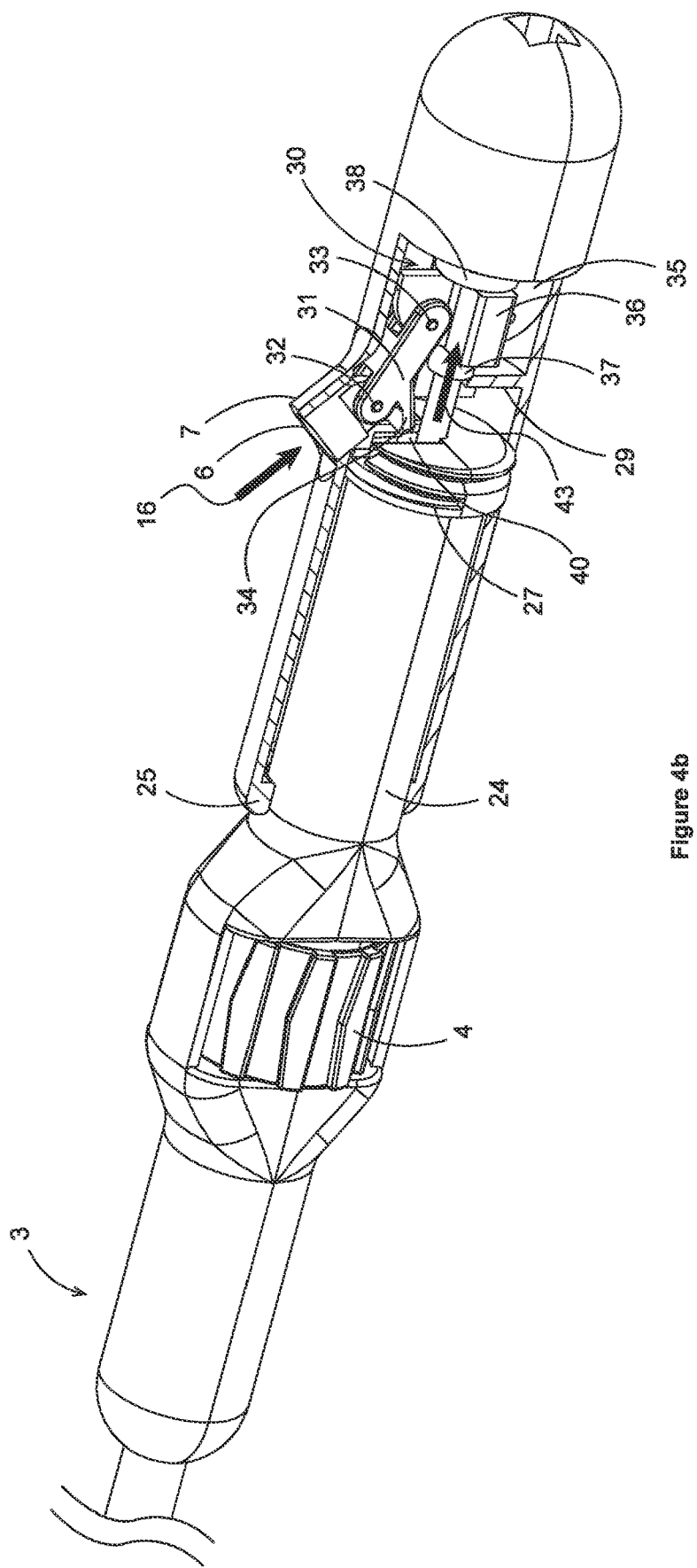
Figure 5:
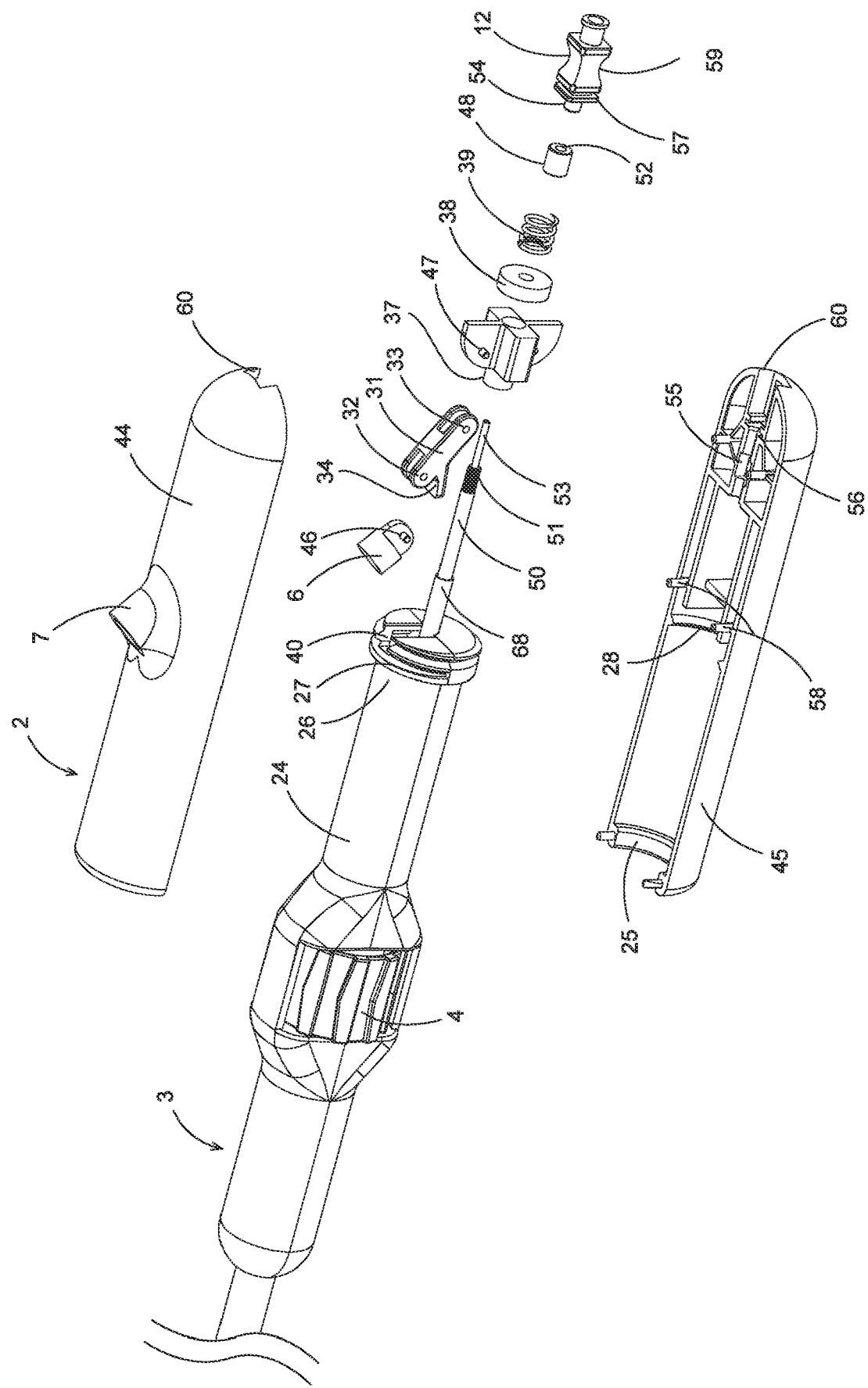
FIG. 5 illustrates an exploded view and internal components of a trans-apical delivery system configured to allow for rapid retraction.

As previously described, a button 6 may be provided which when pushed as depicted by the arrow indicating translation 16 of the button 6, may transmit force and motion along the shaft of the button 6, and through a linkage arm 31, thereby applying it to the catheter carriage 30 and causing it to translate proximally, as depicted by the arrow indicating translation 43 of the catheter carriage 30. Directional control of the translation of the button 6 may be provided by the button housing 7, which may be cylindrically shaped and acts as a piston chamber to guide the similarly cylindrically shaped, piston-like button 6. Functionally, the combination of button 6, linkage arm 31 and catheter carriage 30 may behave as a mechanical linkage. The transmission of force and motion between these components can be achieved through pin-and-hole connection of each successive component to the next; whereas a plurality of button pins 46 (FIG. 5) on one end of the button 6 may be concentrically mated with the distal pin-holes 32 of the linkage arm 31, and a plurality of catheter carriage pins 47 (FIG. 5) on one end of the catheter carriage 30 may be concentrically mated with the proximal pin-holes 33 of the linkage arm 31. The catheter carriage 30 has several characteristics that may assist in its ability to translate smoothly without binding or cocking within the proximal external handle 2. For example, the catheter carriage 30 may have a plurality of support bosses 36 (best seen in FIG. 4A) that can allow the carriage to slide within the proximal external handle 2 by contacting the inner surface of said proximal external handle 2. The catheter carriage 30 may also have a plurality of support fins 35 that can also assist the sliding of the carriage within the proximal external handle 2 by contacting the inner surface of said proximal external handle 2. Additionally, the plurality of support fins 35 may also provide locations for the plurality of catheter carriage pins 47 (FIG. 5).

In order to provide the necessary return force for appropriate valve-capturing ability through the distal end of the bell catheter 10, a cylindrical retaining nut 38 may be in contact with both the catheter carriage 30 and a compression spring 39. This compression spring 39 can act to push the catheter carriage 30 and bell catheter 10 proximal end 68 and distal end towards the dilating tip 9 when the button is released due to the bias provided by the compression spring 39 causing the bell catheter distal end 10 to slide over top of the anchoring catheter anchoring tip 23.

Figure 3B:
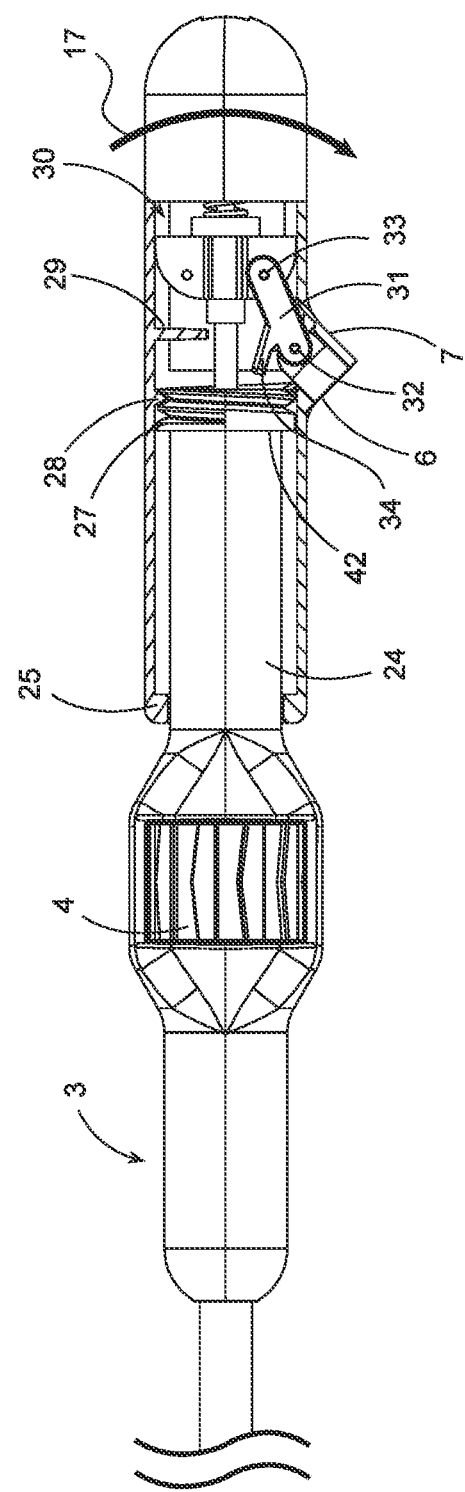
Figure 3C:
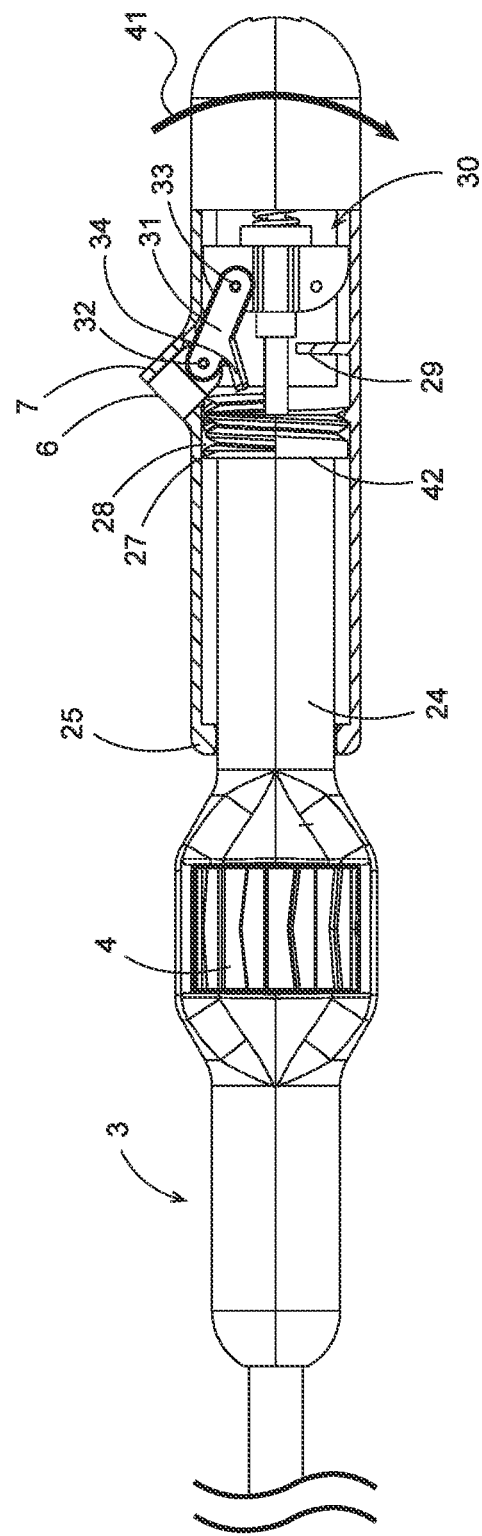
Figure 3D:
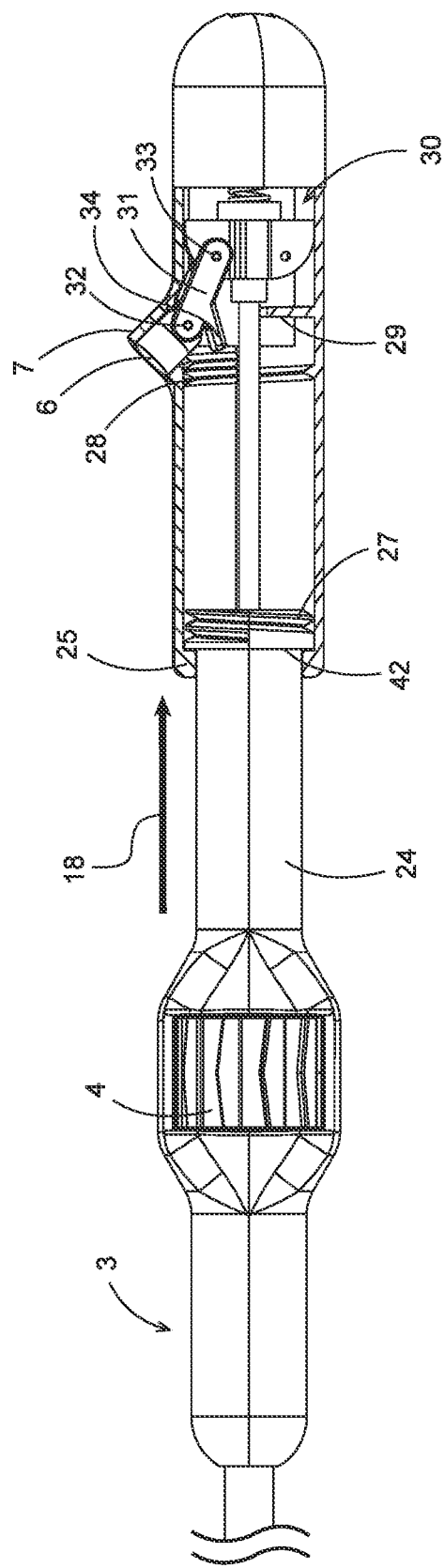

Continuing on through the sequence of views of an operational sequence of a trans-apical delivery system that is configured to allow for rapid retraction of the delivery system 1, by turning to FIG. 3B it is shown that further rotation of the proximal external handle 2 as depicted by the arrow indicating rotation 17, may allow the external threads 27 of the middle section of the internal handle 24 and internal threads 28 of the proximal external handle 2 to further become disengaged. If this rotation is continued (arrow indicating continued rotation 41 of the proximal external handle 2, FIG. 3C), the above mentioned threads may eventually completely disengage, as illustrated in FIG. 3D. Once the above mentioned threads are completely disengaged, the proximal external handle 2 may be free to translate away from the distal handle 3 when pulled proximally by an operator, as depicted by the arrow indicating translation 18 of the proximal external handle 2. The proximal end of the dilator tip may now be butted up against the distal end of the delivery catheter 8 forming a smooth continuous outer surface, and all catheters may be nested within one another. This can complete the rapid retraction process, whereupon the device can safely be removed from the apex of a patient's heart (not shown) or another treatment site. It should be noted that the internal circular rib 25 located on the distal end of the proximal external handle 2 may acts as a rigid, physical stop upon contact with the external circular flange 42 located at the proximal end of the middle section 24 of the internal handle. This limits the translation of the proximal external handle 2 and associated components relative to the internal handle, ensuring the handles do not become fully detached from one another.

As mentioned previously, there is an internal slot 40 (FIG. 4A) located at the proximal-most end of the middle section of the internal handle 24. The purpose of this internal slot 40 is to provide space wherein a rectangular tab 34 of the linkage arm 31 may be placed to prevent unwanted rotation of the proximal external handle 2 relative to the inner handle 24 or distal handle 3, and the relationships between these components is more easily appreciated when witnessed as depicted in FIG. 4A. The rectangular tab may be biased to rest in the slot when the button remains undepressed. One further feature of the mechanical linkage defined by the button 6, linkage arm 31 and catheter carriage 30 that must be appreciated may be realized by the pressing of the button 6, whereupon the rectangular tab 34 of the linkage arm 31 becomes fully removed from the internal slot 40, and full rotation of the proximal external handle 2 relative to the inner handle 24 is thus enabled.

Turning now to FIG. 5, there is illustrated an exploded view with internal components of a trans-apical delivery system configured to allow for rapid retraction of delivery system 1. While many of the elements of FIG. 5 have been previously described herein, additional detail will now be given with emphasis to certain elements used to anchor components within the handle. The proximal external handle 2 may be comprised of two handle halves, specifically an upper section 44 and a lower section 45 which may be fastened together by way of commonly used medical device adhesives such as cyanoacrylate UV cure adhesives that may be applied to a plurality of pegs 58 for mating of said proximal external handle sections 44, 45. Other means for coupling the two handle halves together include but are not limited to press fits, screws, ultrasonic welding, etc. The pegs 58 are illustrated as being located within the lower section 45 of the proximal external handle 2, and each peg may have a complementary boss having an aperture into which it fits in the upper section 44, although it is not shown. The relative positions of the pegs and bosses may be transposed. At the proximal-most end of each of the sections (upper 44, and lower 45) of the proximal external handle 2 there is illustrated a plurality of rectangular slots 60 that may act to securely locate and retain the body 59 of the connector such as needle hub 12. Additionally, a plurality of pockets 56 for retaining the needle hub flange 57 may be provided in close proximity to the plurality of rectangular slots 60, in order to retain and locate a specific fastening feature of the needle hub 12, being primarily the needle hub flange 57. Also found within the upper section 44 and lower section 45 of the proximal external handle 2 may be a plurality of rectangular pockets 55, which serve to locate and retain the anchoring nut 48 and also provide location for an adhesive bond that secures the anchoring nut into the handle sections. It will be remembered that the anchoring nut 48 may provide mechanical fastening and location of the anchoring catheter 50 by way of an externally threaded portion 51 on the anchoring catheter 50 and an internally threaded portion 52 within the anchoring nut 48.

Figure 6:
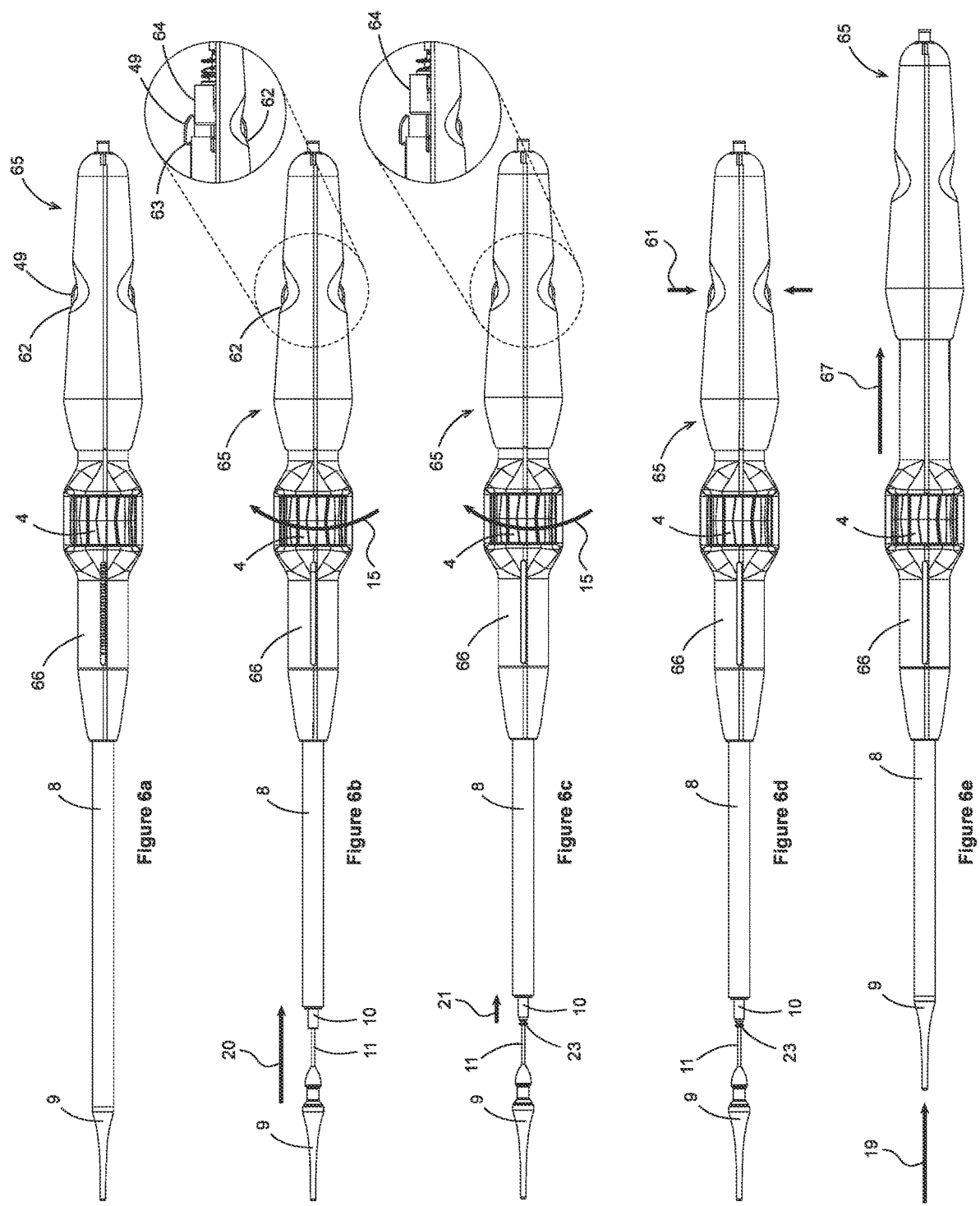
FIGS. 6A-6E illustrate schematic side views of an operational sequence of an alternate embodiment of a trans-apical delivery system configured to allow for rapid retraction.

FIGS. 6A-6E provide illustration of an operational sequence of an alternate embodiment of a trans-apical delivery system 1 configured to allow for rapid retraction. FIG. 6A depicts the first view of an operational sequence, showing another embodiment of a proximal external handle 65. In this embodiment of a proximal external handle 65, rapid retraction may be provided by way of a similar fashion as previously described herein, but with alternative means for disengagement of the proximal external handle 65 from another embodiment of a distal handle section 66. Specifically, the actuator mechanism in this embodiment may include latching buttons 49 (FIG. 6A-6C) which may be used to maintain this embodiment of the distal handle section 66 coupled to this embodiment of the proximal external handle 65. The latching buttons 49 may be in continuous and flexible connection with this embodiment of the distal handle section 66, but may be typically located within a recess of the proximal external handle embodiment 65. Thus, an interfering edge 63 of the latching buttons may be registered against another interfering edge 62 that is within the proximal external handle embodiment 65, prior to engagement. As depicted in FIG. 6D, once both the latching buttons 49 are depressed (illustrated by arrows 61 indicating translation/bending of the cantilevered latching buttons 49) the interfering edge 63 of the buttons may achieve clearance of the interfering edge 62 of the proximal external handle 65 by bending flexion (FIG. 6E). Clearance between the components may allow for translation of this embodiment of the proximal external handle 65 away from this embodiment of the distal handle 66, as depicted by directional arrow 67 indicating translation of the proximal external handle embodiment 65 (FIG. 6E). The remaining internal and external elements of this embodiment (FIG. 6A-6E) of a trans-apical delivery system 1 may be configured to allow for rapid-retraction are as that of the delivery system described in the '964 patent.

Figure 7:
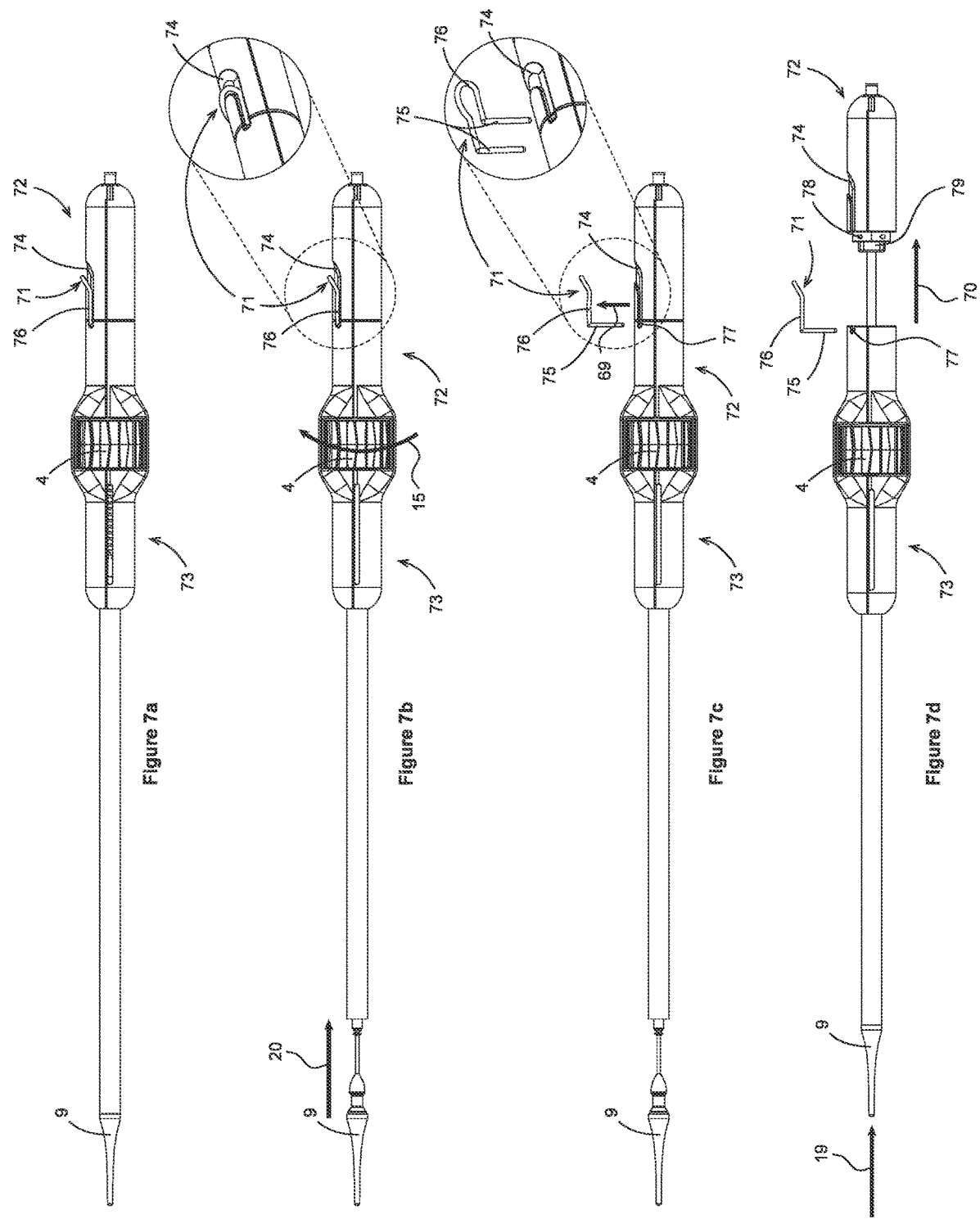
FIGS. 7A-7D illustrate schematic side views of an operational sequence of another alternate embodiment of a trans-apical delivery system configured to allow for rapid retraction.

FIGS. 7A-7D provide illustration of an operational sequence of yet another alternate embodiment of a trans-apical delivery system 1 configured to allow for rapid retraction. FIG. 7A depicts the first view of an operational sequence, showing yet another embodiment of a proximal external handle 72. In this embodiment of a proximal external handle 72, rapid retraction may be provided by way of a similar fashion as previously described herein, but with alternative means for disengagement of the proximal external handle 72 from yet another embodiment of a distal handle section 73. In the embodiment illustrated in FIG. 7A, a retaining pin/latch style of handle retention similar to what may be seen in the modern hand-grenade may be provided. Specifically, a retaining pin 71 which may be comprised of a preferential shaped wire-form having a grasping portion 76 and shafts 75 (FIG. 7C) may be used to pin a proximal external handle section embodiment 72 to a distal handle embodiment 73 by disposing the shafts 75 in receiving pin holes 77 (located on the proximal end of the distal handle embodiment 73) and pin holes 78 (located on the proximal handle embodiment 72). A recess 74 (FIG. 7B) in the handle for the retaining pin 71 may provide a location for the pin to sit flush with the outer surface of the proximal handle embodiment 72, preventing the snagging of sterile gloves that may be adorned by the clinical user (not shown). Operation of the actuation mechanism here having a retaining pin 71 may be as follows: after final deployment of a prosthetic heart valve (not shown) by sustained rotation of the thumbwheel 4 (FIG. 7B), the user may then grasp the retaining pin 71 and pull it out of the recess 74 as depicted by directional arrow 69 indicating translation of the retaining pin 71. Once the retaining pin shafts 75 are entirely removed from the pin holes 77, 78, the proximal external handle embodiment 72 may become free to translate away from the distal handle embodiment 73 as depicted by directional arrow 70 indicating translation of the proximal external handle embodiment 72. The remaining internal and external elements of this embodiment (FIG. 7A-7D) of a trans-apical delivery system 1 may be configured to allow for rapid-retraction are as that of the delivery system described in '964 patent.

Prosthesis

Figure 8:
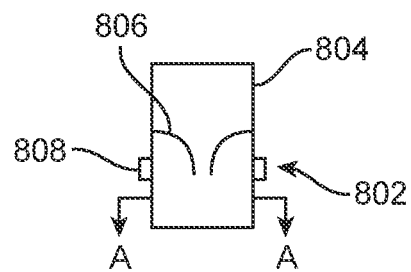
FIG. 8 illustrates a schematic diagram of an exemplary prosthesis

FIG. 8 illustrates a schematic diagram of an exemplary prosthesis 802 which may be used with any of the delivery catheters disclosed herein. The prosthesis 802 is preferably a prosthetic valve such as a prosthetic mitral valve, although it may be a prosthetic valve for any other region in the body such as a prosthetic triscuspid valve, a prosthetic aortic valve, or a prosthetic pulmonary valve. Or it may be a prosthetic venous valve, or any other prosthetic valve, or prosthetic device. The prostheses 802 preferably includes an expandable frame 804 with a prosthetic valve mechanism 806 and preferably includes an anchor mechanism 808. The expandable frame may be balloon expandable or self-expanding and the frame expands into engagement with the native valve. The prosthetic valve mechanism 806 may include one, two, three, or more prosthetic valve leaflets which have an open position which allows antegrade fluid flow therepast, and a closed configuration where the prosthetic valve leaflets coapt with one another to prevent or minimize retrograde fluid flow therepast. The fluid may be blood or another body fluid. The prosthetic leaflets may be pericardial tissue or other tissues, or they may be formed from synthetic materials such as polymers or metals. The anchor mechanism may be any structure configured to help engage tissue and anchor the prosthesis with the native valve.

Figure 9A:
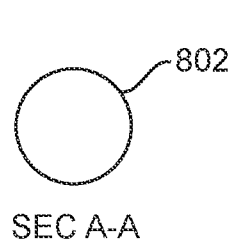
FIGS. 9A-9B illustrate exemplary cross-sections of the prosthesis in FIG. 8.
Figure 9B:
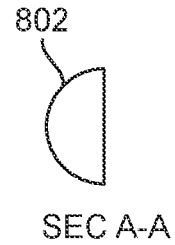

FIGS. 9A-9B illustrates taken along the line A-A in FIG. 8 and show possible cross-sections of the frame 804. FIG. 9A shows that the prosthesis may have a circular cross-section, and in preferred embodiments, preferably for the mitral valve, the prosthesis may have a D-shaped cross-section so that the prosthesis conforms to the native anatomy. Additional details about exemplary embodiments of a prosthesis are disclosed in the '964 patent previously incorporated herein by reference.

Figure 10A:
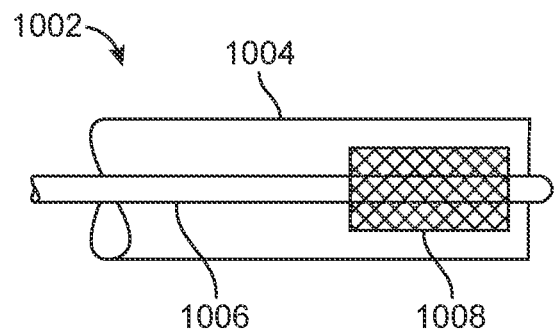
FIGS. 10A-10B illustrate a prosthesis coupled to a delivery catheter.
Figure 10B:
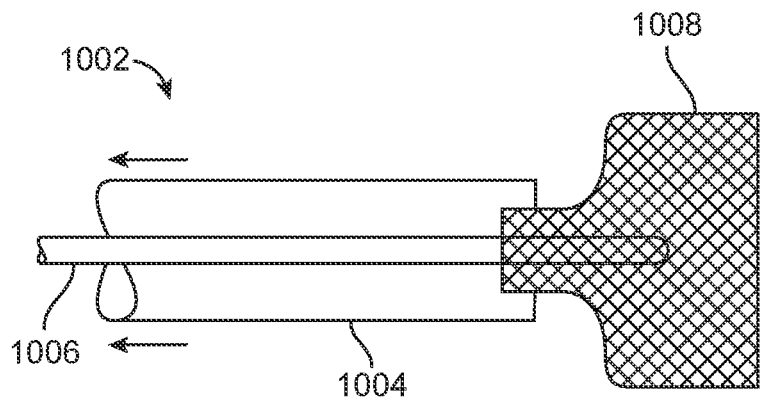

FIGS. 10A-10B illustrate a prosthesis 1008 such as the one described in FIG. 8 coupled to a delivery catheter 1002. In FIG. 10A, the prosthesis is in a collapsed configuration and being carried and constrained by the delivery catheter 1002. The delivery catheter 1002 may be any of the delivery catheters described herein. An outer sheath 1004 constrains the prosthesis 1008 and keeps it in the collapsed configuration and disposed over an inner shaft 1006 slidably disposed in the outer sheath 1004. The inner shaft 1006 may be any of the inner shafts disclosed herein including the bell catheter previously disclosed. Other optional shafts in the delivery catheter are not illustrated for convenience. As the outer sheath 1004 is retracted proximally, or the bell catheter is advanced distally, the prosthesis becomes unconstrained from the outer sheath and begins to self-expand as seen in FIG. 10B. Once the prosthesis is completely unconstrained, is self-expands into position, preferably into engagement with a native valve.

Delivery

Figure 11:
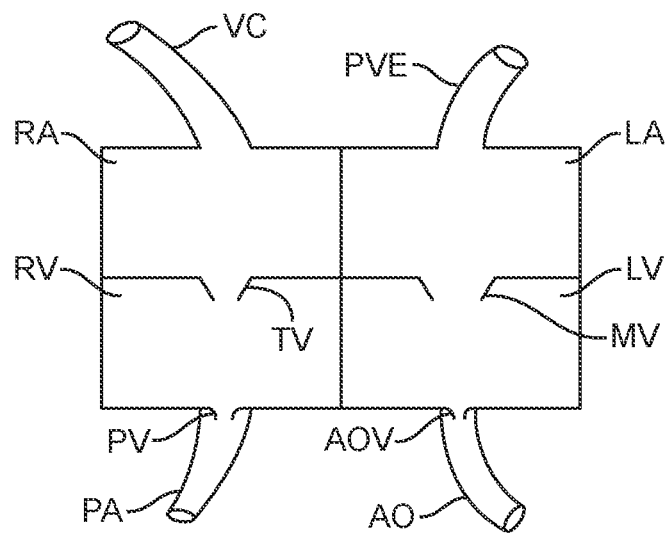
FIG. 11 illustrates basic human heart anatomy.

FIG. 11 illustrates basic human heart anatomy. The heart includes four chambers, the right atrium RA, the right ventricle RV, the left atrium LA, and the left ventricle LV. Several valves prevent retrograde blood flow. The tricuspid valve TV controls flow from the right atrium to the right ventricle, and the pulmonary valve PV controls flow out of the right ventricle RV. The mitral valve MV controls flow between the left atrium LA and the left ventricle LV, and the aortic valve AOV controls flow out of the aorta AO. The major vessels coupled to the heart include the vena cava VC which brings venous blood back to the right atrium RA, and the pulmonary artery brings blood from the right ventricle RV to the lungs (not illustrated). Oxygenated blood from the lungs returns to the left atrium LA via the pulmonary veins PVE, and blood is delivered out of the left ventricle LV to the body by the aorta AO.

Figure 12A:
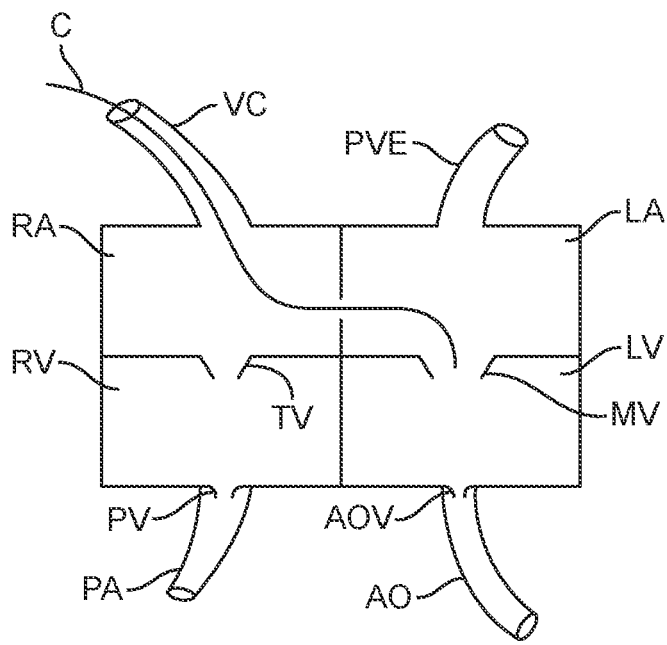
FIGS. 12A-12C illustrate exemplary delivery methods.

FIG. 12A illustrates one exemplary delivery method for treating mitral valve MV. In this embodiment, the delivery catheter C which may be any of the delivery devices disclosed herein and may have any of the prostheses disclosed herein is advanced typically from a femoral vein in the groin up into the vena cava VC into the right atrium RA and then transseptally across the atrial septal wall into the left atrium LA and then downward into disposition across or adjacent the native mitral valve MV where the prosthesis may be deployed as described herein.

Figure 12B:
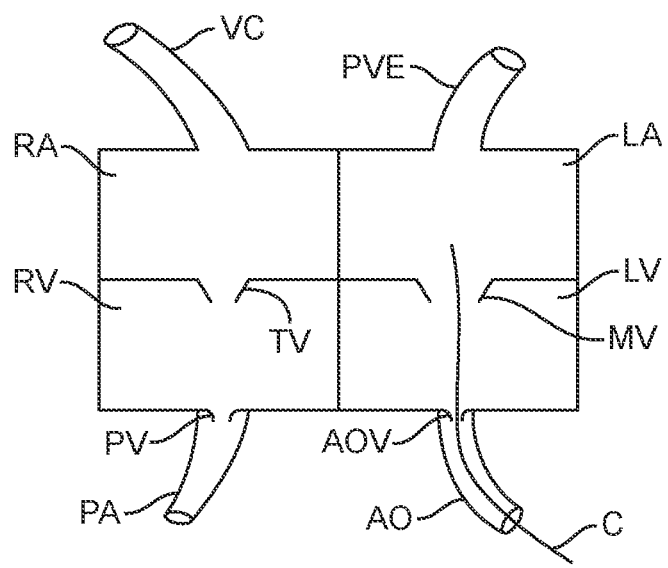

FIG. 12B illustrates another exemplary delivery method for treating a mitral valve MV. In this embodiment, the delivery catheter C which may be any of the delivery devices disclosed herein and may have any of the prostheses disclosed herein is advanced typically from a femoral artery or other artery (e.g. radial artery) up into the aorta AO in to the left ventricle LV and then across the mitral valve MV or adjacent thereto for deployment of the prosthesis as described herein.

Figure 12C:
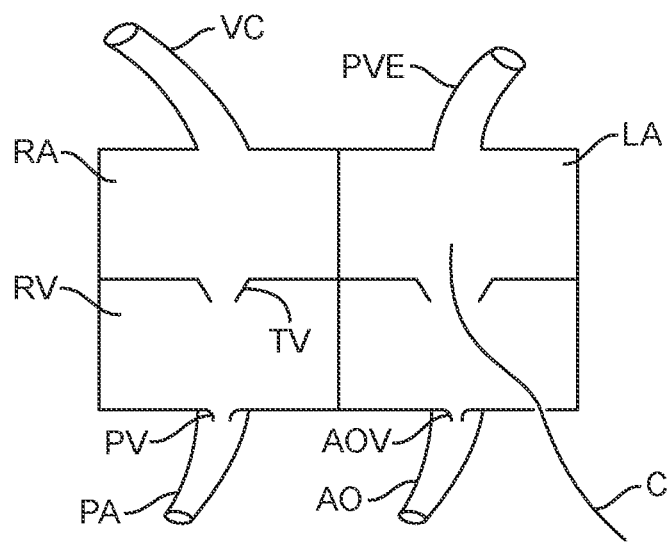

FIG. 12C illustrates another exemplary delivery method for treating a mitral valve MV. In this embodiment, the delivery catheter C which may be any of the delivery devices described herein and may have any of the prostheses disclosed herein is typically advanced transapically from outside the body, through the chest well, into the apex of the heart into the left ventricle LV and then adjacent or across the mitral valve MV where the prosthesis is then deployed as disclosed herein.

Figure 13A:
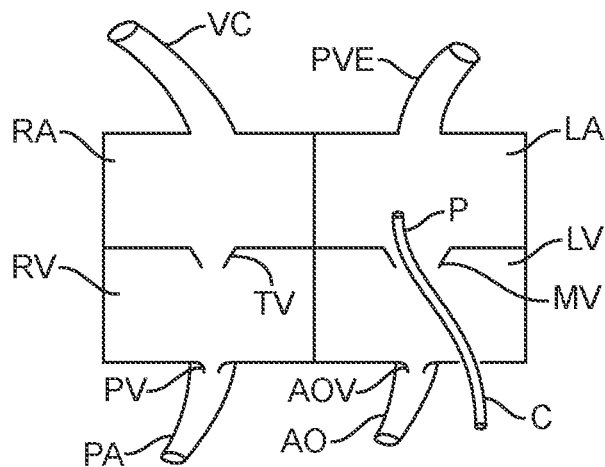
FIGS. 13A-13C illustrate an exemplary method of deploying a prosthesis in the heart.
Figure 13B:
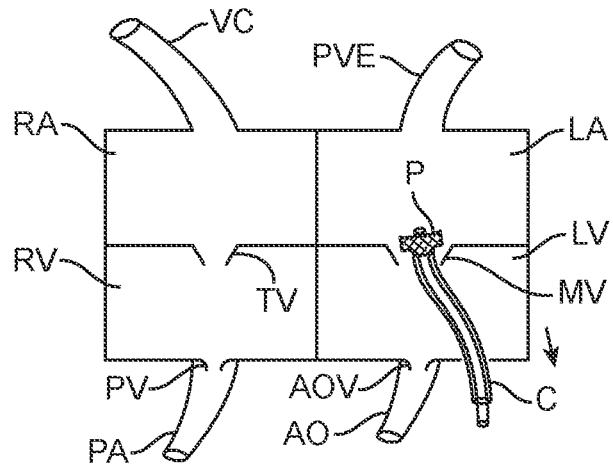
Figure 13C:
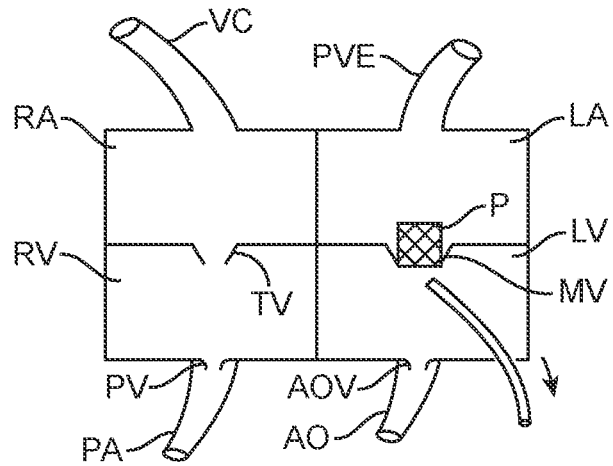

FIGS. 13A-13C illustrate an exemplary method of deploying a prosthesis P in the heart using a delivery catheter C which may be any of the delivery devices disclosed herein. The prosthesis is preferably a mitral valve prosthesis but may be any of the prostheses disclosed herein. In FIG. 13A, the delivery catheter is preferably delivered transapically to the mitral valve MV. In FIG. 13B, once the prosthesis P has been properly positioned relative to the native mitral valve MV, the outer sheath is retracted proximally (or the inner bell shaft is advanced distally) so that the prosthesis is unconstrained and allowed to self-expand into engagement with the native mitral valve and anchor into position. After the prosthetic valve has been deployed and properly positioned and anchored, the delivery catheter is then retracted proximally and removed from the heart as seen in FIG. 13C. The prosthetic valve now takes over the function of the native mitral valve allowing antegrade flow from the left atrium to the left ventricle and preventing or minimizing regurgitation of blood from the left ventricle to the left atrium.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery device for delivering a prosthesis, the device comprising:
   a delivery catheter configured to carry a prosthesis therein;
   a dilator catheter disposed in the delivery catheter and having a tapered distal tip coupled thereto;
   a rapid retraction mechanism for controlling movement of the delivery catheter relative to the tapered distal tip, wherein:
   the rapid retraction mechanism comprises an inner handle threadably connected to an outer handle, and
   the rapid retraction mechanism is configured to threadably decouple the inner handle from the outer handle such that the outer handle is proximally retractable relative to the inner handle to abut a proximal end of the tapered distal tip against a distal end of the delivery catheter.

2. The device of claim 1, further comprising a first actuation mechanism for controlling movement of the delivery catheter, wherein actuation of the first actuation mechanism moves the delivery catheter away from the prosthesis thereby at least partially removing a constraint therefrom.

3. The device of claim 2, further comprising a deployment mechanism for controlling release of the prosthesis from an anchoring catheter, the anchoring catheter disposed at least partially in the delivery catheter, and wherein actuation of the deployment mechanism moves the anchoring catheter away from the prosthesis thereby releasing a constraint therefrom.

4. The device of claim 2, wherein the first actuation mechanism comprises a thumbwheel.

5. The device of claim 2, wherein the deployment mechanism comprises an actuatable button with a linkage coupled thereto.

6. The device of claim 1, wherein the rapid retraction mechanism comprises a release mechanism, the actuation of which threadably decouples the inner handle from the outer handle.

7. The device of claim 6, wherein the release mechanism comprises a button.

8. The device of claim 1, wherein the rapid retraction mechanism comprises a screw thread and interference member configured to constrain movement of the rapid retraction mechanism.

9. The device of claim 1, wherein the rapid retraction mechanism comprises a flexible interference member configured to be deflected to release the rapid retraction mechanism.

10. The device of claim 1, wherein the rapid retraction mechanism comprises a pin and a pin-hole link, wherein the pin is configured to be removed from the pin-hole link to release the rapid retraction mechanism.

11. The device of claim 1, wherein the proximal end of the tapered distal tip abutted against the distal end of the delivery catheter forms a smooth continuous outer surface on the delivery device.

12. A system comprising:
   a prosthesis;
   a delivery device comprising:
   a delivery catheter configured to carry the prosthesis therein;
   a dilator catheter disposed in the delivery catheter and having a tapered distal tip coupled thereto;
   a rapid retraction mechanism for controlling movement of the delivery catheter relative to the tapered distal tip, wherein:

the rapid retraction mechanism comprises an inner handle threadably connected to an outer handle, and the rapid retraction mechanism is configured to threadably decouple the inner handle from the outer handle such that the outer handle is proximally retractable relative to the inner handle to abut a proximal end of the tapered distal tip against a distal end of the delivery catheter.

13. The system of claim 12, wherein the prosthesis comprises a prosthetic heart valve.

14. The system of claim 13, wherein the prosthetic heart valve comprises a mitral valve or a tricuspid valve.

15. The system of claim 12, wherein the rapid retraction mechanism comprises a release mechanism, the actuation of which threadably decouples the inner handle from the outer handle.

16. The system of claim 12, wherein the release mechanism comprises a button.

17. The system of claim 12, wherein the rapid retraction mechanism comprises a screw thread and interference member configured to constrain movement of the rapid retraction mechanism.

18. The system of claim 12, wherein the rapid retraction mechanism comprises a flexible interference member configured to be deflected to release the rapid retraction mechanism.

19. The system of claim 12, wherein the rapid retraction mechanism comprises a pin and a pin-hole link, wherein the pin is configured to be removed from the pin-hole link to release the rapid retraction mechanism.

20. The system of claim 12, wherein the proximal end of the tapered distal tip abutted against the distal end of the delivery catheter forms a smooth continuous outer surface on the delivery device.

21. The system of claim 12, further comprising a first actuation mechanism for controlling movement of the delivery catheter away from the prosthesis, wherein the first actuation mechanism comprises a thumbwheel.

22. The system of claim 12, further comprising a deployment mechanism for controlling release of the prosthesis from an anchoring catheter, the anchoring catheter disposed at least partially in the delivery catheter, and wherein actuation of the deployment mechanism moves the anchoring catheter away from the prosthesis thereby releasing a constraint therefrom.

23. The system of claim 22, wherein the deployment mechanism comprises an actuatable button with a linkage coupled thereto.

* * * * *